(12) United States Patent
Almasri et al.

(10) Patent No.: US 12,723,985 B2
(45) Date of Patent: Sep. 1, 2026

(54) MULTIPLEX PLASMONIC SENSORS ON THE LONGITUDINAL SIDE OF AN OPTICAL FIBER

(71) Applicant: The Curators of the University of Missouri, Columbia, MO (US)

(72) Inventors: Mahmoud Almasri, Columbia, MO (US); Jiayu Liu, Columbia, MO (US); Sura Muhsin, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 316 days.

(21) Appl. No.: 18/170,815

(22) Filed: Feb. 17, 2023

(65) Prior Publication Data

US 2023/0258568 A1 Aug. 17, 2023

Related U.S. Application Data

(60) Provisional application No. 63/311,106, filed on Feb. 17, 2022.

(51) Int. Cl.
*G01N 21/65* (2006.01)
*B01L 9/00* (2006.01)
(Continued)

(52) U.S. Cl.
CPC ......... *G01N 21/658* (2013.01); *G01N 21/554* (2013.01); *G01N 33/54373* (2013.01);
(Continued)

(58) Field of Classification Search
CPC ............... G01N 21/658; G01N 21/554; G01N 33/54373; G01N 33/5438;
(Continued)

(56) References Cited

U.S. PATENT DOCUMENTS 7,102,747 B2 * 9/2006 Wang .................. G01N 21/658
356/301
9,488,583 B2 * 11/2016 Baets .................. G01N 21/658
(Continued)

FOREIGN PATENT DOCUMENTS

CN 103630493 A * 3/2014 ........... G01N 21/658
CN 105651738 A * 6/2016 ........... G01N 21/553
(Continued)

OTHER PUBLICATIONS

Cennamo, Nunzio, et al. “Design of surface plasmon resonance sensor in plastic optical fibers based on nano-antenna arrays.” Procedia Engineering 168 (2016): 880-883. (Year: 2016).*
(Continued)

*Primary Examiner* — Michael A Lyons
*Assistant Examiner* — Noah J. Haney
(74) *Attorney, Agent, or Firm* — Sandberg Phoenix & von Gontard P.C.

(57) ABSTRACT

A plasmonic sensor achieving high sensitivities by using a metallized nanoantennae array patterned on the longitudinal side of a fiber optic cable is disclosed herein. The sensor is capable of single and multiplex detection of biomarkers, viruses, food and waterborne pathogens, proteins, and other chemical and biological specimens. Plasmonic sensor embodiments including SERS and RI sensing arrays are disclosed.

19 Claims, 22 Drawing Sheets

(51) Int. Cl.
*G01N 21/25* (2006.01)
*G01N 21/552* (2014.01)
*G01N 33/543* (2006.01)
*G02B 6/02* (2006.01)

(52) U.S. Cl.
CPC .......... *G01N 33/5438* (2013.01); *B01L 9/527* (2013.01); *C12Q 2565/628* (2013.01); *C12Q 2565/632* (2013.01); *G01N 2021/258* (2013.01); *G02B 6/0229* (2013.01); *G02B 6/02295* (2013.01); *G02B 6/02314* (2013.01); *G02B 6/02319* (2013.01)

(58) Field of Classification Search
CPC .............. G01N 2021/258; B01L 9/527; C12Q 2565/628; C12Q 2565/632; G02B 6/0229; G02B 6/02295; G02B 6/02314; G02B 6/02319
USPC .......................................................... 356/301
See application file for complete search history.

(56) References Cited

U.S. PATENT DOCUMENTS 10,274,492 B2 4/2019 Almasri et al.
10,989,867 B2 4/2021 Kinzel et al.
2007/0109544 A1* 5/2007 Chau .................... G01N 21/554 356/445
2008/0166706 A1* 7/2008 Zhang ............. G01N 33/54313 977/924
2010/0128275 A1* 5/2010 Chau .................. G01N 21/7703 977/954
2012/0050732 A1* 3/2012 Lu .......................... B82Y 40/00 427/205
2012/0212732 A1* 8/2012 Santori ............. G01N 21/7703 977/954
2015/0211993 A1* 7/2015 Chau .................... G01N 21/554 356/445
2017/0328836 A1* 11/2017 Lu .......................... G02B 6/032
2018/0364223 A1* 12/2018 Fretes .................. G01N 21/554
2020/0326475 A1* 10/2020 Kinzel .................. G03F 7/2016
2021/0364510 A1* 11/2021 Lin ........................ G02B 6/122

FOREIGN PATENT DOCUMENTS

CN 108896528 A * 11/2018 ........... G01N 21/658
CN 109085141 A * 12/2018 ........... G01N 21/553
CN 109580578 A * 4/2019 ......... G02B 6/02052
CN 110596051 A * 12/2019 ........... G01N 21/554
CN 111272703 A * 6/2020 ............. G01N 21/41
CN 211528212 U * 9/2020 ........... G01N 21/552
KR 20160056218 A * 5/2016 ........... G01N 21/554

OTHER PUBLICATIONS

Esfahani Monfared, Yashar. "Overview of recent advances in the design of plasmonic fiber-optic biosensors." Biosensors 10.7 (2020): 77. (Year: 2020).*

Cheng, Zhan, et al. "Au-nanoshells modified surface field enhanced LRSPR biosensor with low LOD for highly sensitive hlgG sensing." Optics & Laser Technology 134 (2021): 106656. (Year: 2021).*

* cited by examiner 110
210
100
200

300

310
300
200

300
320

MULTIPLEX PLASMONIC SENSORS ON THE LONGITUDINAL SIDE OF AN OPTICAL FIBER

CROSS-REFERENCE TO RELATED APPLICATIONS

The present application claims priority benefits from U.S. provisional patent application Ser. No. 63/311,106 filed Feb. 17, 2022.

FIELD

The present teachings relate to chemical and biological sensing technologies, and particular to devices fabricated to sense chemical and biological analytes with surface plasmonic sensor techniques including surface enhanced Raman spectroscopy and surface plasmon resonance refractive index sensing.

BACKGROUND

The statements in this section merely provide background information related to the present disclosure and may not constitute prior art.

The rapid, accurate detection of contaminants and pathogens (collectively referred to hereinafter as 'analytes') is a motivating force for countless industries, health institutions, and governments. Ideally, such detection would allow for the containment and control of such dangerous analytes.

In many cases, the tests currently relied upon to detect such contaminants and pathogens are themselves riddled with faults and weaknesses. Testing by the sampling and cultivation of bacterial cultures, for example, can take up to five days, and requires sending a sample to a laboratory staffed by trained personnel. Enzyme-linked immunosorbent assay (ELISA) testing can be relatively quick and easy for the patient, but also relies on sending samples to laboratories with often long turnaround times, and furthermore is restricted only to detecting antibodies generated by a patient's immune system. Polymerase chain reaction (PCR) tests can have high false-negative and false-positives rates.

High false-negative and false-positive rates in any tests are an effect of the tests' selectivity and sensitivity. Selectivity refers to any test's ability to identify a particular analyte without confusing it with other analytes. Selectivity is frequently a matter of degree. In scientific and clinical practice, selectivity is typically a statistical measure that states the probability of a 'negative' test outcome resulting from a genuine absence of the analyte.

Furthermore, sensitivity refers to the minimum quantity of material required before a test can 'detect' that material. Although PCR tests are often praised for their sensitivity, they are often found to have an insufficient test sensitivity. In scientific and clinical practice, sensitivity is also a typically statistical measure that states the probability of a 'positive' test outcome resulting from a genuine presence of the analyte.

One promising approach to increasing the selectivity and sensitivity of prevailing detection methods employs the use of surface plasmon phenomena in sensing techniques. Surface plasmons are coherent, delocalized oscillations of electrons often found at particular material interfaces such as the interface of a metal and a dielectric material like air or water. Sensors that take advantage of surface plasmon phenomena are hereinafter called plasmonic sensors.

One such plasmonic sensor is the 'refractive index' sensor, a brief description of which follows. The oscillatory nature of surface plasmons allows them to undergo excitation by absorbing photons from a beam of light that impinges on the material interface at particular wavelengths to achieve resonance with the surface plasmons. The conditions at which maximum resonance occurs are controlled by, among other things, the material composition of the interface and the wavelength of incidence of the impinging light. Thus, with all other conditions being equal, as the material composition of the interface changes, so will the wavelength at which the impinging beam of light achieves maximum resonance with the surface plasmons.

This change in the wavelength of maximum resonance resulting from a change of material composition at the interface is understood as a consequence of the change in the local refractive index at the interface. Thus, adsorption of a chemical or biological specimen of interest onto the interface will change the local refractive index and, consequently, the wavelength of maximum resonance for the impinging beam of light. Careful measurement of this change in local refractive index permits one to sense the presence of biological and chemical species of interest at the interface. Sensors that take advantage of this resonance phenomenon are hereinafter referred to as "refractive index" (RI) sensors.

Another technique that takes advantage of surface plasmon phenomena is surface-enhanced Raman spectroscopy (SERS). Raman spectroscopy uses light to probe molecular vibrations. Photons of light are applied to a sample, and these then interact with various excitations in the sample. The result is a spectral "fingerprint" that provides specific information on the molecular composition of the sample. The selectivity benefits of a sensor that detects biological or chemical specimens of interest using Raman spectroscopy are clear: anything in a sample with a different molecular makeup than the analyte of interest will generate a different Raman 'fingerprint,' making it far more difficult to spoof such a detector with 'false positives.'

The sensitivity of Raman spectroscopy was very low for a long time after its initial development simply because the proportion of applied photons that successfully undergo Raman interactions with a sample was typically very small. However, this has changed with the advent of Surface-Enhanced Raman Spectroscopy (SERS) that greatly amplified the sensitivity of Raman Spectroscopy. SERS is performed at the surface of a material (in other words, the interface of two materials). The 'enhancement' of SERS is believed to come substantially from excitation of surface plasmons by the light applied to the sample. Unlike in RI sensing, however, this resonance is used to enhance SERS signals for generating spectra characteristic of specimens of interest, and not specifically or directly to gauge a change in an interface's local refractive index induced by such specimens of interest.

Both SERS and RI sensing technologies can use a surface-bound 'detection layer' to enhance their selectivity. Such a detection layer serves to improve binding of the biological or chemical specimen of interest to the interface. For example, an interface capable of surface plasmon excitation can have antibodies deposited on it, and these antibodies can then further selectively bind only to particular viruses of interest.

Despite the advantages provided by SERS, scientists and engineers have struggled to develop SERS analyte sensors that have extremely high sensitivity and selectivity, but have inexpensive construction and rapid multiplex detection at the point of care. Thus, there exists a need in the art for a sensor design, and fabrication method thereof, that can achieve these goals.

BRIEF SUMMARY

In various embodiments, presented herein is a plasmonic sensor for chemical and biological specimens that comprises an array of metallized nanoantennae patterned on a polished longitudinal side of an optical fiber. The sensor is capable of single as well as multiplex detection of specimens such as biomarkers for cancer detection, viruses, foodborne and waterborne pathogens, and proteins at concentrations as low as $10^{-15}$ M. Crucially, patterning the longitudinal side rather than the tip of an optical fiber allows for a greater surface area for the nanoantennae array, leading to stronger signals being generated. Also disclosed herein, in various embodiments the plasmonic sensor can be embedded in a microfluidic housing that uses dielectrophoretic focusing and trapping to better enable detection of specimens even in very dilute solutions.

The sensor of the present disclosure works by permitting specimens of interest to pass close to, or make contact with, the array of metallized nanoantennae patterned on the longitudinal side of the optical fiber. The array of metallized nanoantennae are similar in the two broad types of plasmonic sensors discussed herein, the SERS sensor and the RI sensor. In the SERS plasmonic sensor embodiments, the array of metallized nanoantennae comprises elevated metallized discs that protrude upward from the polished longitudinal side surface of an optical fiber. In the RI plasmonic sensor embodiments, the array of metallized nanoantennae comprises holes that pass through a metallized layer and end on the polished longitudinal surface of an optical fiber.

The operational principles of SERS and RI plasmonic sensors are distinct, but have similarities. In the case of the plasmonic sensor using SERS, light traveling through the optical fiber arrives at the discs in the array of metallized nanoantennae formed on the longitudinal side of the optical fiber, interacts with the specimens of interest adsorbed on or near those discs to produce characteristic Raman scattering signals indicative of the specimens' unique vibrational modes. This Raman scattering response is dramatically enhanced by the increased surface area of metallized nanoantennae on the longitudinal side of the optical fiber, and this dramatically enhanced signal reflects back through the optical fiber and to a detector. In the case of a plasmonic sensor using RI sensing, when light traveling through the optical fiber arrives at the array of metallized nanoantennae, it resonates with the surface plasmons such that the resonance maximum occurs at a wavelength that shifts with changes in the local refractive index induced by specimens of interest adsorbing on or near the array of metallized nanoantennae.

Also disclosed herein is an inexpensive method for fabrication of the plasmonic sensor disposed on the longitudinal side of a fiber optic and a microfluidic housing for the sensor. Fabrication of the sensor itself can take advantage of several inexpensive and robust techniques, including standard electroplating and microsphere lithography. Thus, fabrication is low-cost and easily scalable while retaining the high selectivity and specificity of SERS spectroscopy. The result is a label free, non-invasive, low cost, point-of-care sensor capable of rapid multiplex detection and identification of chemical and biological specimens. Even in the most complex embodiments disclosed herein, detection times can be under ten minutes from the point of sample introduction.

BRIEF DESCRIPTION OF THE DRAWINGS

Corresponding reference numerals will be used throughout the several figures of the drawings.

DETAILED DESCRIPTION

Figure 1:
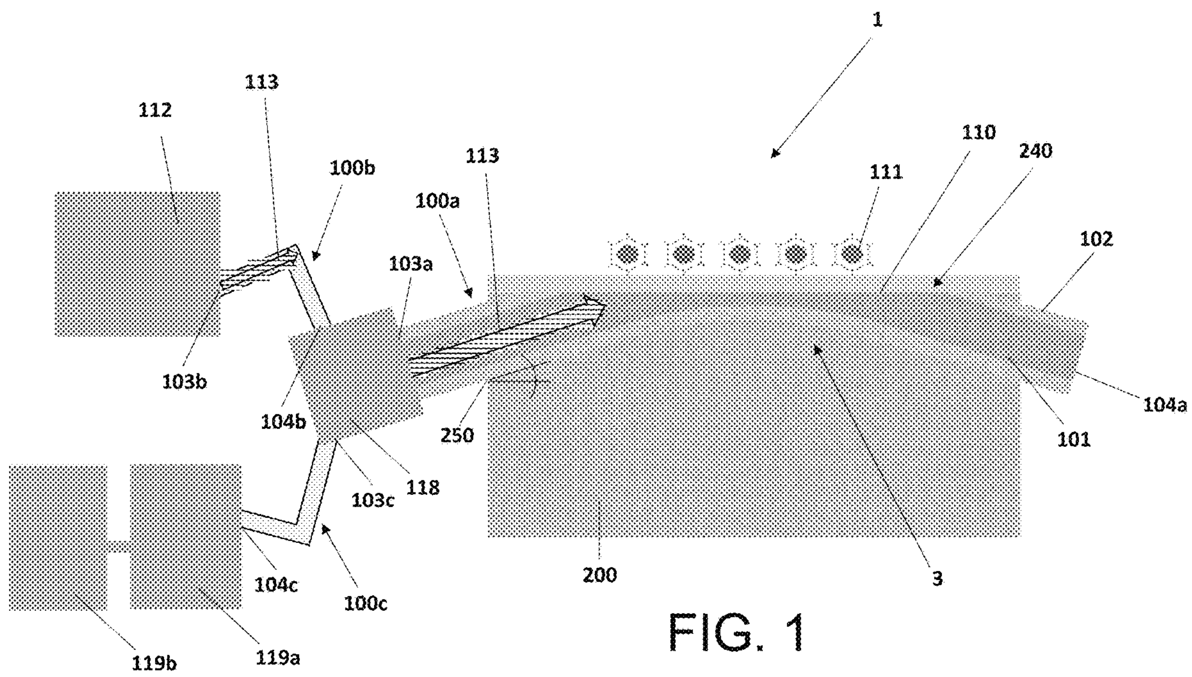
FIG. 1 exemplarily illustrates an optical fiber-based plasmonic sensor system structured and operable to detect chemical or biological specimens of interest that adsorb onto or near a metallized nanoantennae array deposited on a polished longitudinal side surface of an optical fiber, in accordance with various embodiments of the present disclosure.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its applications to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

The terms "plasmonic" and "plasmonic sensor" as used herein refer to sensors that in some way take advantage of the phenomenon of surface plasmons.

The terms "sensor" and "detector' are used interchangeably herein to refer to a device that is capable of generating a signal to indicate the presence of a particular biological or chemical specimen.

The term "SERS" as used herein is an acronym referring to Surface Enhanced Raman Scattering.

The terms "optical fiber" and "fiber optic" as used herein refer to a broad class of fibers typically made of glass or plastic and designed to transmit light between the two ends of the fiber by means of a phenomenon known as total internal reflection.

The terms "nanoantenna" and "nanoantennae" as used herein refer to features of an array that can be either holes present in a conductive layer or discs protruding upward from a conductive layer, and whose scale is suitably measured in nanometers.

The term "microfluidic" as used herein refers to techniques or apparatuses that attempt to exert precise control over the flow of fluids and typically include small, micron-scale manipulations or features.

The term "photoresist" as used herein refers to both 'positive' and 'negative' photoresists, with necessary distinctions provided either explicitly or by context.

The term "optical detector" as used herein refers to any device known in the art to be capable of the collection of optical information, such as light. An optical detector can be but need not be independently capable of digitization or other processing of that information, and no limits on the type or content of optical information are implied herein unless otherwise stated.

The following detailed description comprises disclosure of three exemplary versions (i.e., embodiments) of an optical fiber-based plasmonic sensor system that is structured and operable to detect chemical or biological specimens of interest that adsorb onto or near a metallized nanoantennae array deposited on the polished longitudinal side surface of an optical fiber. In all embodiments, the system, and particularly a plasmonic sensor thereof, is relatively easy and inexpensive to manufacture. For instance, by forming the array of metallized nanoantennae on the polished longitudinal side of the optical fiber, the sensor can achieve a higher surface area (and concomitant higher signal strength) than is seen when such a metallized nanoantennae array is instead deposited on a tip of the optical fiber.

More specifically, referring to FIG. 1, the present disclosure generally provides an optical fiber-based plasmonic sensor system 1 that is structured and operable to detect chemical or biological specimens of interest that adsorb onto or near a metallized nanoantennae array deposited on a polished longitudinal side surface of an optical fiber. The plasmonic sensor system 1 generally comprises a plasmonic sensor 3, an optical fiber 100*a* that is embedded into a support base 200 and then polished and patterned to create a surface having a plurality, e.g., an array, of nanoantennae 240 formed thereon or therein. The optical fiber 100*a* comprises a core 101 and a cladding 102 as well as a first end 103*a*, a second end 104*a*, and a diameter 115. A section of a longitudinal side the core 101 is exposed as a flat surface 110 and is polished and enhanced with the metallized nanoantennae array 240. The plasmonic sensor system 1 additionally includes a laser source 112, an optical coupler 118, an optical detector 119*a* and computer-based processing system 119*b*. As described in detail below, the laser source 112 is structured and operable to provide laser light signal 113 into the first end 103*a*, to which the laser source 112 is operably coupled, optical coupler 118 is structured and operable to guide the light generated by the laser source 112 into and out of the optical fiber 100*a*, the optical detector 119*a* is structured and operable to detect light exiting the optical fiber 100*a*, and the computer-based processing system 119*b* is structured and operable to execute analysis software, via a processor of the computer-based processing system 119*b*, whereby characteristics of the light received at the optical detector 119*a* is analyzed to detect various chemical or biological attributes contained in a specimen that has been placed in contact with the plasmonic sensor 3.

The present disclosure is generally organized first into a discussion of plasmonic SERS sensors followed by a discussion of variations that incorporate IR sensing instead of SERS sensing. The first SERS version (i.e., embodiment)

disclosed herein, which focuses on and details a streamlined optical fiber-based SERS sensor, is exemplarily illustrated in FIGS. 1A-3B. During use, this first sensor version is typically either immersed in a solution containing a specimen of interest or a droplet of the solution is deposited directly on the metallized nanoantennae array 3. The second SERS version (i.e., embodiment), which retains core sensing elements of the first embodiment but introduces microfluidic housing for sample delivery, is exemplarily illustrated in FIGS. 4A-4C. This version allows for a solution containing a specimen of interest to flow directly over the metallized nanoantennae array 240. This can be useful in cases where it is ideal to allow a greater volume of a sample solution to pass over the metallized nanoantennae array 240 and thereby provide more opportunity for biological and chemical specimens of interest to adsorb onto the metallized nanoantennae array 240, where they can be detected.

The third SERS version (i.e., embodiment), which retains both microfluidic housing and the core sensing elements of the prior two embodiments, further introduces electromagnetic focusing and trapping as well as dedicated waste lines for dilute sample solutions, is exemplarily illustrated in FIGS. 5-8F. The electromagnetic focusing present in this third version uses dielectrophoretic forces to concentrate a biological or chemical sample of interest along a flow path toward the metallized nanoantennae array. This third version's electromagnetic trapping, meanwhile, uses dielectrophoretic forces to slow the flow of a biological or chemical sample of interest while it is positioned over the metallized nanoantennae array, thereby better enabling adsorption of such specimens onto the metallized nanoantennae array.

Following discussion of these three SE RS embodiments, an embodiment of the metallized nanoantennae array 240 that allows for RI sensing is disclosed, along with an exemplary fabrication thereof. The functions and methods of use of each described version are provided after their respective methods of fabrication.

Figure 1A:
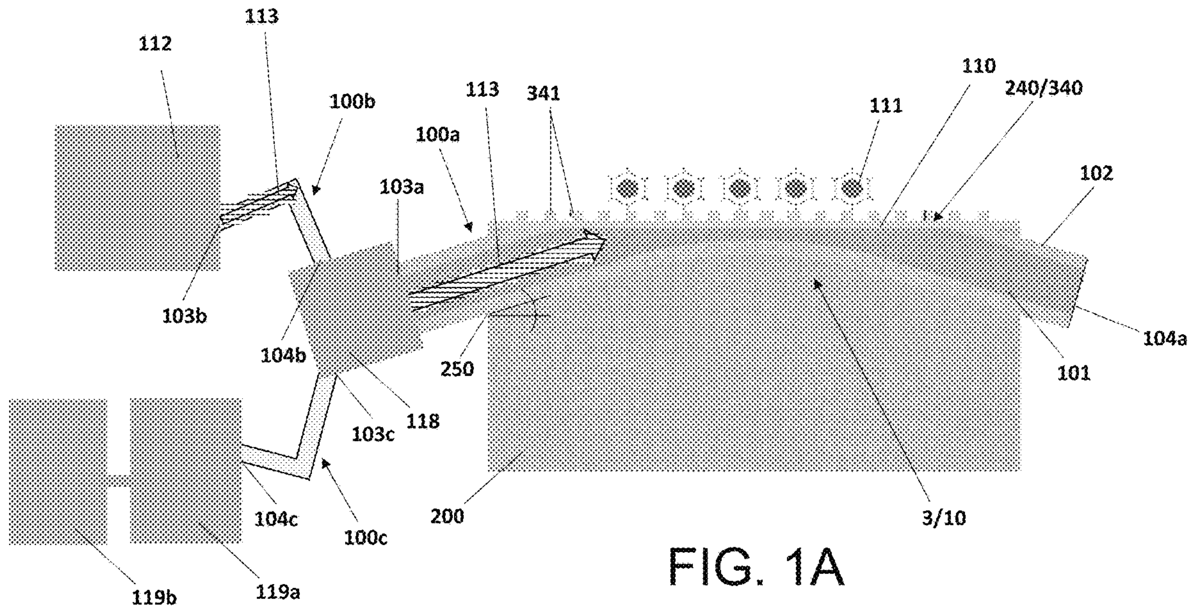
FIG. 1A shows the optical fiber-based plasmonic sensor system shown in FIG. 1, comprising an exemplary plasmonic SERS sensor fabricated on the longitudinal side of an optical fiber embedded in a support base, jn accordance with various embodiments of the present disclosure.
Figure 1B:
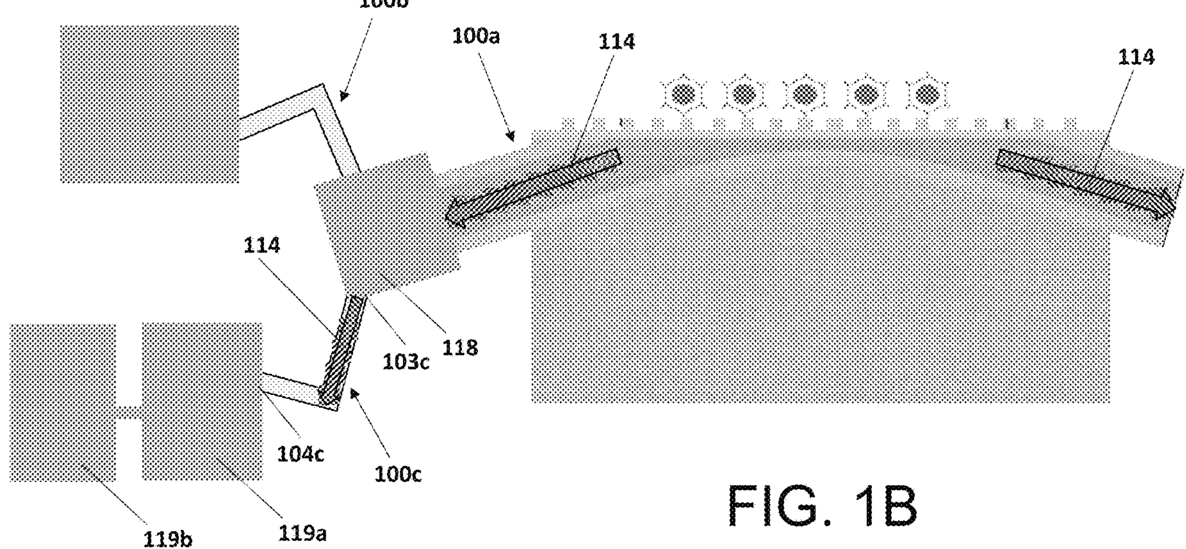
FIG. 1B shows a similar depiction of the diagrammatic depiction of SERS on an exemplary plasmonic SERS sensor fabricated on the longitudinal side of an optical fiber embedded in a support base shown in FIG. 1A, but demonstrates how Raman signals, once generated and reflected, are acquired, in accordance with various embodiments of the present disclosure.
Figure 1C:
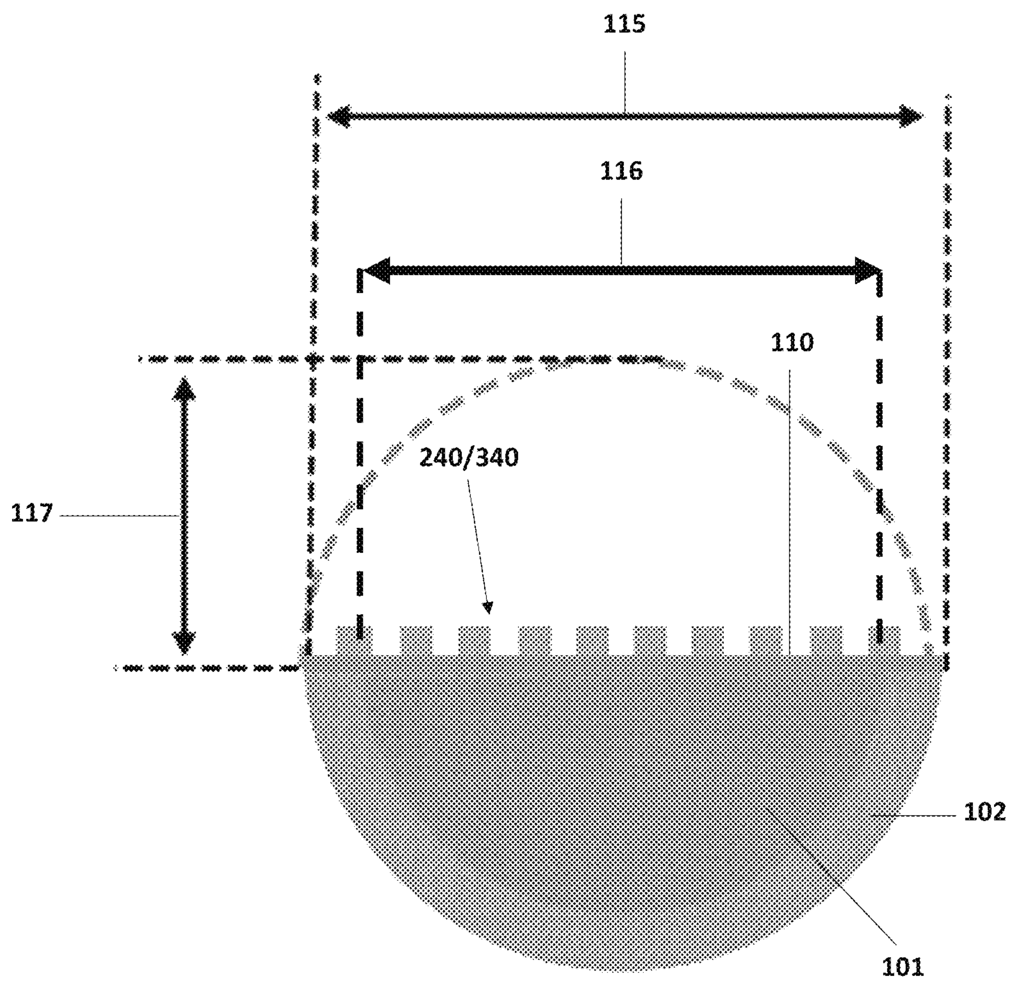
FIG. 1C provides an exemplary cross-sectional view of the optical fiber shown in FIG. 1A that has been polished and has had a metallized nanoantennae array deposited on it, jn accordance with various embodiments of the present disclosure.

Referring now to FIGS. 1A-1C, in various embodiments, the SERS sensor system 1 that comprises a SERS sensor 10. The SERS sensor 10 comprises an optical fiber 100*a* that is embedded into a support base 200 and then polished and patterned to create a surface that is structured and operable to enhance Raman scattering. The optical fiber 100*a* comprises a core 101 and a cladding 102 as well as a first end 103*a*, a second end 104*a*, and a diameter 115. A section of a longitudinal side the core 101 is exposed as a flat surface 110 and is polished and enhanced with the metallized nanoantennae array 240, referred to in the SERS embodiments as the metalized nanoantenna array 340, comprising a pattern of individual nanoantennae, which in various embodiments comprise metallized nano sized discs 341. The optical fiber is positioned at an angle 250 relative to the flat surface 110, and in various embodiments the angle can be between zero and ninety degrees, for example fifteen degrees. The laser source 112 is structured and operable to provide laser light 113 into the first end 103*a*, to which the laser source 112 is operably coupled. In the exemplary embodiment depicted in FIGS. 1A-1B, the laser source 112 is operably coupled to first end 103*a* by an inlet fiber 100*b* and an optical coupler 118. The laser source 112 can provide laser light having any desired intensity or frequency suitable to induce excitation of a biological or chemical sample of interest. For example, in various embodiments, the laser source can generate laser light having a wavelength of between 300 nm and 800 nm. For example, in various instances the laser source can generate laser light having a wavelength of 532 nm. In various exemplary embodiments, the plasmonic sensor 3 can further comprise an external housing designed and disposed to aid in controlled deposition of a liquid sample onto the metallized nanoantennae array 240, for example by syringe, according to means known in the art.

Figures 2A, 2B, 2C, 2D:
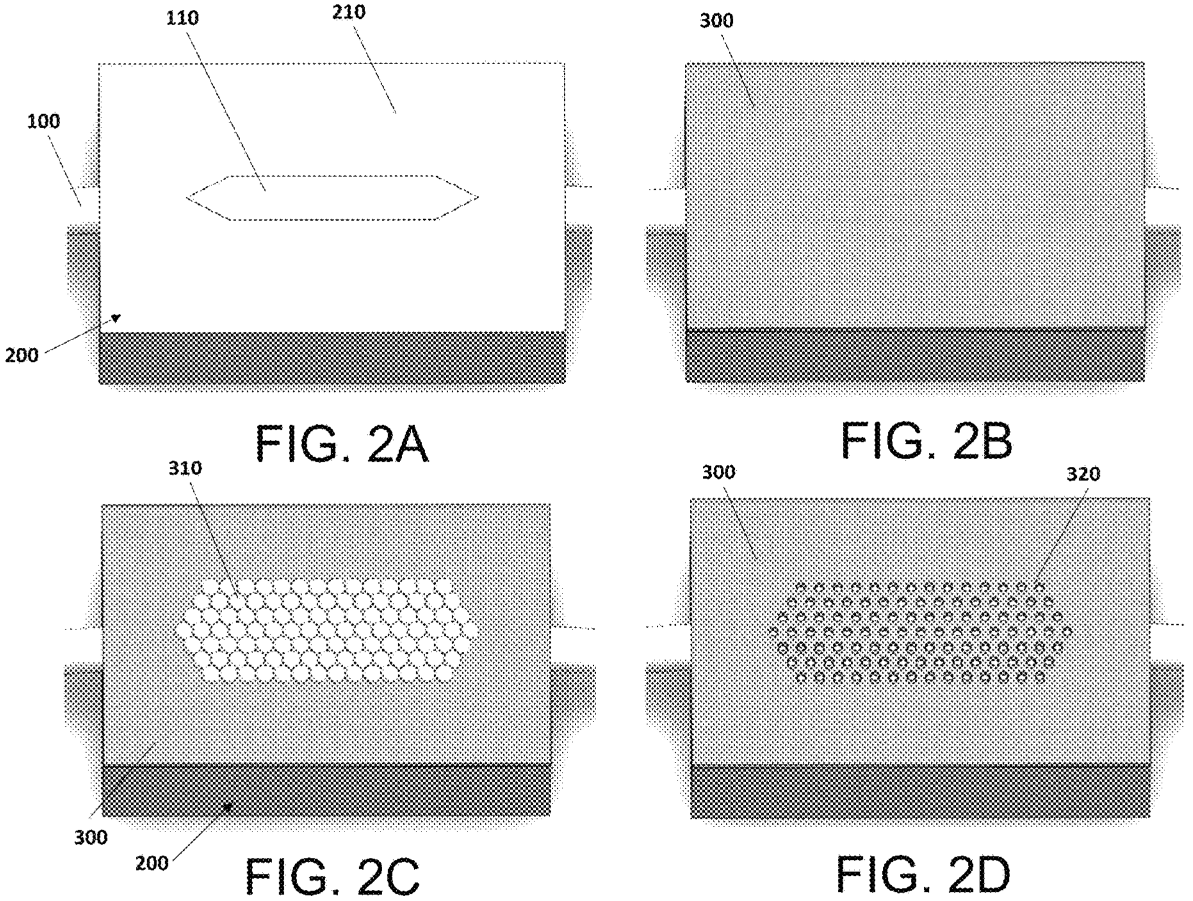
FIGS. 2A-2F provide a depiction of an exemplary sequence of steps for fabricating a SERS plasmonic sensor on the longitudinal side of an optical fiber that is embedded in a support platform, such as that shown in FIG. 1A, jn accordance with various embodiments of the present disclosure.

FIGS. 2A-2F exemplarily depict a fabrication process of the sensor depicted in FIGS. 1A-C, in accordance with various embodiments of the present disclosure. FIG. 2A shows an optical fiber 100*a* embedded in a support base 200. In various embodiments, the support base 200 is cast or printed around a section of the optical fiber 100*a*. An upper or first surface 210 of the support base 200 is then polished, abrading away layers of the upper or first surface 210 until a surface 110 of the optical fiber core 101 is exposed and is coplanar with the polished/abraded support base upper surface 210. The size (e.g., the diameter) 115 of the optical fiber 100*a* can vary. Ideally, the depth 117 (FIG. 1C) of abrasion into the fiber is such that the exposed surface 110 of the optical fiber core 101 is maximized. This occurs when the depth 117 of abrasion is substantially equivalent to one half of the fiber diameter 115, resulting in a surface 110 that has a width 116 equivalent to the diameter of the core 101 as this maximizes the exposed fiber optic surface area of the core 101, which in turn enhances the SERS signal. For example, in various instances, the optical fiber diameter 115 can be 105 μm, and polishing can proceed to a depth of approximately 52.5 μm into the optical fiber 100*a*, resulting in a polished exposed optical fiber section 101 having a surface area of several square centimeters. Although polishing is exemplarily described above to abrade the optical fiber 100*a* to approximately one half its diameter 115, it is envisioned that the optical fiber 100*a* can be polished or abraded to any desirable depth such that the width 116 of the surface 110 can have any desired dimension and remain within the scope of the present disclosure.

After the upper surface 210 and the optical fiber 100*a* have been polished as described above, a layer of positive photoresist 300 is then applied atop the upper surface 210, as shown in the exemplary depiction in FIG. 2B. The layer of positive photoresist 300 is a light sensitive material that can in various embodiments be a polymeric mixture that weakens when exposed to light of particular frequencies and intensities. After weakening, a developer can be applied to the photoresist to wash away the 'weakened' areas while retaining the non-weakened areas. Many different chemical arrangements of positive photoresist and corresponding developer are known in the art, and the use of any is considered to be within the scope of the present disclosure. An array of spheres, called microspheres 310, is then applied atop the photoresist 300 for lithography. The array of spheres can have any desired size, shape and/or diameter suitable to the desired arrangement and size of nanoantennae in the metallized array 340. For example, in various embodiments the microspheres 310 can be spherical and have a diameter between 0.1 microns to 3.0 microns, e.g., in various instances 1.0-1.5 microns. Alternatively, it is envisioned that the microspheres 310 can have any other desired shape and size and remain within the scope of the present disclosure. In various embodiments, the microspheres 310 can be fabricated of silica, polystyrene, or any other material known in the art to be transparent to ultraviolet (UV) light. After being applied to the layer of photoresist 300, the microspheres 310 self-assemble into a close-packed hexagonal arrangement as seen in FIG. 2C. The microspheres 310 serve as optical elements through which ultraviolet (UV) light can be focused to create patterns in the photoresist 300. The particulars of the arrangement of microspheres 310 and the angle and intensity of impinging UV light can result in a wide array of varying pattern types, as has been established in U.S. Pat. No. 10,989,867, which is herein incorporated herein by reference in its entirety. The practice of using self-assembling microspheres and UV light to selectively pattern photoresist is known as "microsphere lithography" (MPL). MPL is an attractive technique for generating controlled patterns in a given substrate because of its low cost and versatility. However, alternative techniques known to those in the art such as e-beam and focused ion beam lithography are considered to be within the scope of this disclosure.

Figures 2E, 2F:
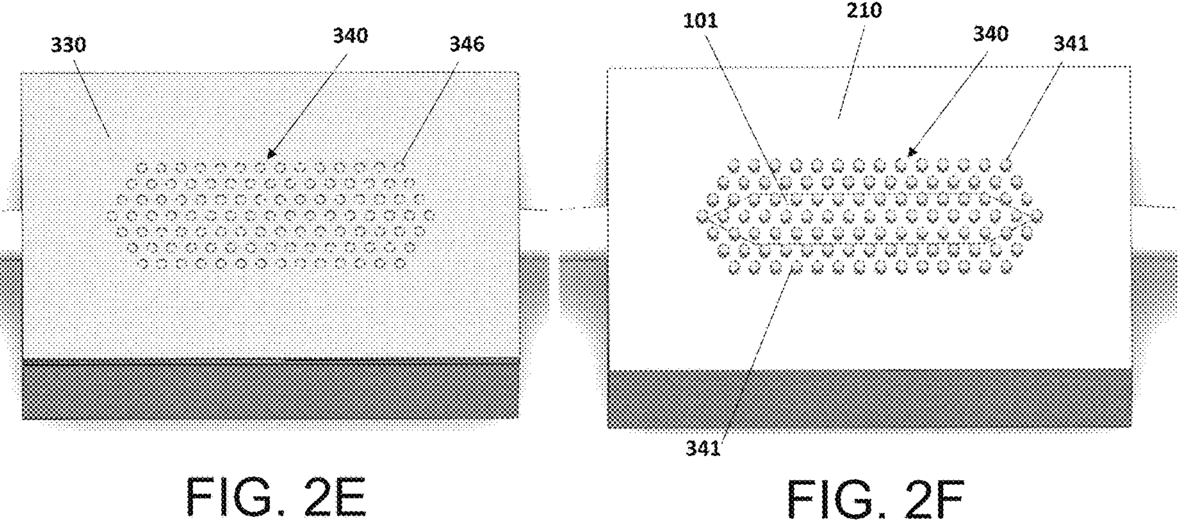

Upon removal of the microspheres 310, via known MPL techniques, an array of holes 320 is generated in the photoresist layer 300 as exemplarily depicted in FIG. 2D. A disc material 330 is then deposited onto to the photoresist layer 300 and holes 320 by sputtering, a technique in which ions of material are ejected from a 'target' and onto a 'substrate.' The disc material 330 is ultimately the material from which the metallized nanoantennae array 340 is made, and thus the material to which the chemical and biological specimen of interest 111 will adsorb. In this exemplary embodiment, the disc material is gold, which is known to strongly contribute to the enhancement of Raman signals that is required in SERS. However, any other metals such as silver, metal alloys, semiconductors, dielectrics, and combinations thereof known to produce surface enhancement of Raman signals are considered to be within the scope of the present disclosure. Note that deposition of the disc material 330 is shown in FIG. 2E to cover the entire photoresist layer 300 as well as the holes 320, thereby filling the holes with disc material and generating the nanoantennae array 340. This generation of the nanoantennae array 340 is the desired result of depositing disc material 330 onto the photoresist layer 300 and holes 320. Thus, coating the entire photoresist layer 300 is not necessary and is shown simply because it is an exemplary approach. Alternative techniques that focus more singularly on depositing disc material substantially or solely in the holes 320 to form the nanoantennae array 340 are considered to be well within the scope of the present disclosure.

Subsequently, the photoresist layer 300 is removed. A selected technique for removal of the photoresist layer 300 can depend on the particular composition of photoresist used, but all appropriate means known in the art, including but not limited to physical removal or 'lift off,' chemical dissolution or 'stripping,' and plasma etching or 'ashing' are considered to be within the scope of the present disclosure. As exemplarily shown in FIG. 2F, after removal of the photoresist layer 300, the base surface 210 is generally exposed resulting in an array of nanoantennae 340 made from disc material 330 being deposited on both apportion of the base surface 210 and the exposed fiber optic core surface 110.

In the exemplary embodiment depicted in FIGS. 2A-2F, the support base 200 is made from is a substantially rigid polymer such as polylactic acid (PLA) or acrylonitrile butadiene styrene (ABS), but can alternately be made of any sufficiently rigid and workable material known in the art. In the exemplary embodiment illustrated in FIG. 2E, the disc material 330 is applied by sputtering, but can be applied by any deposition technique known to the art, including but not limited to chemical vapor deposition, molecular beam epitaxy, electroplating, and/or any combination thereof.

Figure 3A:
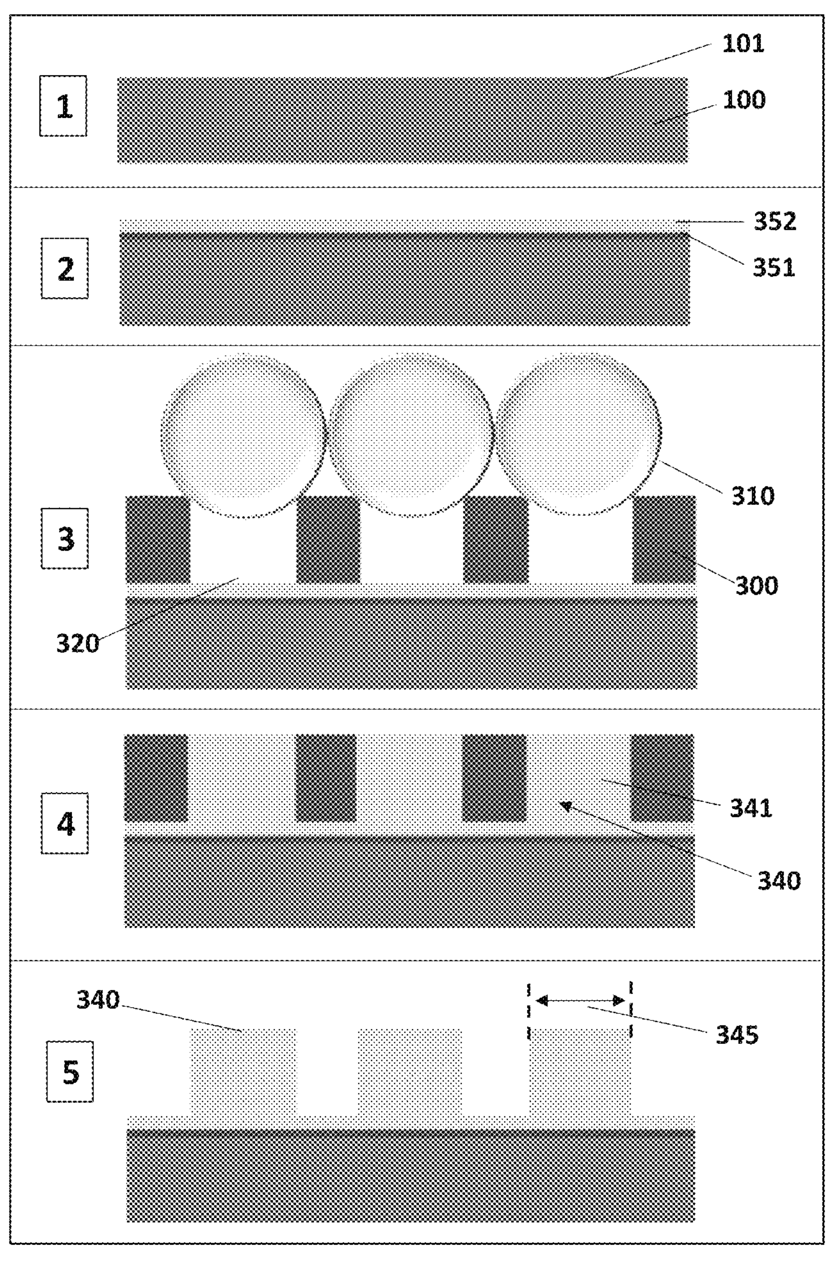
FIG. 3A provides depiction of an exemplary alternative sequence of steps for fabricating a SERS plasmonic sensor on the longitudinal side of an optical fiber, such as that shown in FIG. 1A, jn accordance with various embodiments of the present disclosure.

Another fabrication method distinct from that presented in FIGS. 2A-2F relies on electroplating to create the metallized nanoantennae array 340 rather than the deposition method described above. Electroplating, in contrast to deposition, is the use of applied electrical potential to deposit metal onto a conductive substrate, and electroplating enables the fabrication of thicker nano sized discs 341 than is generally able to be achieved by sputtering or other means of vacuum deposition. Briefly described here and in FIG. 3A by example, the fabrication process begins by embedding and polishing the optical fiber 100, which is shown from the side, in zoomed-in cross section, in FIG. 3A box 1. The optical fiber 100*a* is still embedded in the support base 200, but the support base is not shown in this zoomed-in figure. An adhesion layer 351 and a seed layers 352 are then deposited on the coplanar optical fiber surface 110 and surface 210 of the support base 200. The adhesion layer 351 is deposited first, followed by the seed layer 352, and both are deposited in sequence by sputtering, chemical vapor deposition, or any other means known in the art. The adhesion layer 351 serves as an intermediary to aid in the binding of the seed layer 352. In various embodiments, the adhesion layer 351 is a layer of chromium between 1 and 100 nm, for example 10 nm, and the seed layer 352 is a layer of gold between 1 and 100 nm, for example 30 nm, as shown in FIG. 3A box 2. Although in this exemplary embodiment the adhesion layer 351 of chromium aids in the binding of the seed layer 352 of gold, alternative embodiments can omit the adhesion layer if direct binding of the seed layer to the surfaces 110 and 210 is adequate. A photoresist layer 300 is then spin-coated atop the seed layer 352 to a thickness that in various embodiments is between 50 nm and 10 μm, for example 500 nm. Microsphere lithography is then performed as described previously, by depositing a self-assembling layer of microspheres 310 and irradiating them with UV light to produce a regular pattern of holes 320, as seen in FIG. 3A box 3.

Figure 3B:
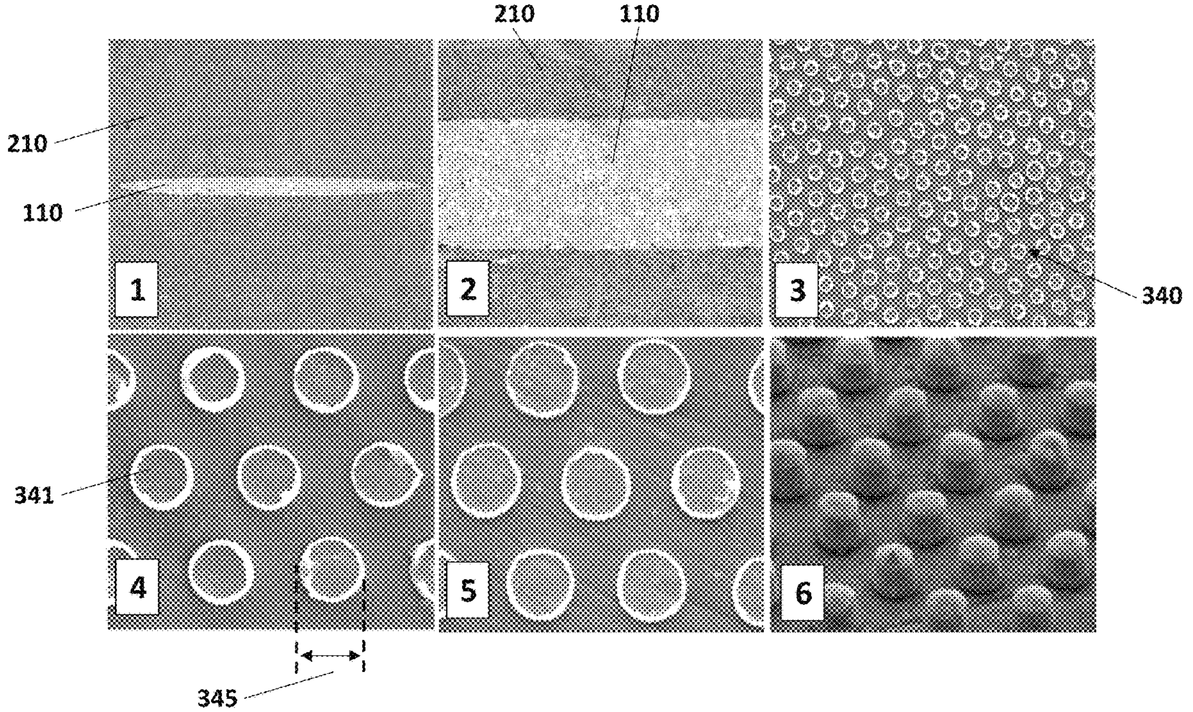
FIG. 3B provides exemplary microscopy photographs of a SERS plasmonic sensor patterned on the longitudinal side of an optical fiber at increasing levels of magnification.

Then, in order to grow the nanoantennae array 340 in the array of holes 320, the seed layer 352 is connected to a power supply and immersed in a gold electroplating solution (not shown). The seed layer function as a working electrode, and a platinum mesh (not shown) is connected to the same power supply and used as a counter electrode. In various embodiments, electroplating can occur at a fixed current for three hours, resulting in a nanoantennae array 340 with a thickness 345 of between 10 nm and 1 μm, for example 500 nm, as seen in FIG. 3A box 4. Finally, the photoresist layer 300 is removed, leaving the array 340. Acceptable variations known to those of ordinary skill are considered to be within the scope of the present disclosure. For example, electroplating could take place at a fixed applied potential rather than a fixed applied current, and the values for current and potential can vary depending on the desire thickness, roughness, and porosity of the applied metal, as well as other considerations such as solution composition and desired electroplating time. The thickness 345 of the discs in the nanoantennae array 340 can also vary. Variations in deposition time can influence the width 345 of individual metallized discs 341, as seen in FIG. 3B boxes 4-5, and as seen in FIG. 3B box 6, electroplating can produce even thicker discs with higher surface area. The metal content and chemical environment of the electroplating solution can vary, as it will dictate disc material 330, and the counter electrode cannot be platinum but instead platinized titanium, iridium oxide, carbon mesh, or any other conductive counter-electrode material known to those of ordinary skill in the art.

FIG. 3B provides photographs of exemplary depictions of the metallized nanoantennae array 340 at increasing levels of magnification as well as depictions of individual discs 341 of varying size. As seen in the exemplary photograph of FIG. 3B, box 1, at insufficient magnification, the metallized discs 341 are not easily visible on the exposed surface of the polished fiber optic 101. FIG. 3B, box 2 shows the exposed surface 110 at greater magnification, but even here, the metallized nanoantennae array 340 is not clearly distinguishable. However, at the magnification present in FIG. 3B, box 3, a regular metallized nanoantennae array 340 becomes discernable. As FIG. 3B, boxes 4-5 show, alterations in UV exposure timing and the extent of disc material 330 deposition can result in controllable variations in the size, shape, and relative positions of each metallized disc 340. Box 6 shows the results of using electroplating to fabricate larger metallized discs 341 than sputtering can generally produce. Although typically featuring diameters less than one micron across, the discs can vary in size to suit the needs of the application. More complex patterns such as those comprising clusters of nanoantennae can be achieved by altering the angle of incidence of the UV light.

Use and operation of the sensor 10 as illustrated exemplarily in FIGS. 1A-1C is as follows. Referring first to FIG. 1A, a biological or chemical specimen of interest 111 is introduced to the metallized nanoantennae array 340 (e.g., the array of nano size discs 341) through a variety of possible means. For example, a droplet of a liquid sample solution containing the specimen of interest 111 can be place on the exposed core surface 110, or the sensor 10 can be immersed in a sample solution containing the specimen of interest. The specimen of interest 111 then comes into contact with and adsorbs onto the metallized discs 341 of the nanoantennae array 340. A laser source 112 emits laser light 113 directly into a first end 103*b* of the ingress fiber 100*b* at a desired wavelength (e.g., a 532 nm wavelength), although the wavelength can vary depending on the application. The laser light 113 travels through the optical fiber 100*b* via total internal reflection and enters an optical coupler 118. The optical coupler 118 diverts the laser light 113 into the first end 103*a* of the optical fiber 100*a* toward the exposed surface 110. At the surface 110, the laser light interacts with the specimen of interest 111 disposed or adhered or surrounding the metalized discs 341, producing Raman scattering signals 114. Surface plasmons present in the metallized nanoantennae array 340 enhance the strength of these signals 114, which then proceed through the core 101 of optical fiber 100*a* toward the first end 103*a* of the optical fiber 100*a*. Optimization of the angle 250 can maximize the extent to which Raman signals 114 are reflected from the exposed surface 110 back toward the first end 103*a*. Turning now to FIG. 1B, from here, the Raman signals 114 proceed back through the optical fiber 100*a*, whereafter the Raman signal 114 returns to the optical coupler 118. The optical coupler 118 diverts the returned Raman signal 114 into a first end 103*c* of an egress fiber 100*c*, and the Raman signal travels from there to a second end 104*c* of the egress fiber. The second end 104*c* of the egress fiber is operatively coupled to the optical detector 119*a*. The optical detector 119*a* receives the Raman signal 114 so that it can be processed. The optical detector 119*a* is communicatively connected, (wire or wirelessly) to the computer-based processing system 119*b* that includes at least one processor.

Processing of the Raman signal 114 exiting the coupler 118 and entering the detector 119*a*, via the computer-based processing system 119*b*, generates a spectrum, the features of which will indicate the identities of one or more chemical and/or biological specimens that adsorbed onto the metallized nanoantennae array 340. In the event that the sample solution does not contain chemical and/or biological specimens that the user was looking for, the spectrum's features will not be inclusive of those features characteristic of the specimen, thus indicating the absence of those specimens.

In various embodiments, ordinary variations can be made that are within the scope of the present disclosure. For example, the second end 104*a* of the optical fiber 100*a* can be operatively coupled to a detector 119*a*. The optical coupler 118 can be operatively connected to a notch filter to spectrally filter the signal 114 before it reaches the detector 119*a*. All means known in the art of acquiring the Raman signal 114 after any number of interactions with the biological or chemical specimen of interest 111 are within the scope of the present disclosure.

Figures 4A, 4B:
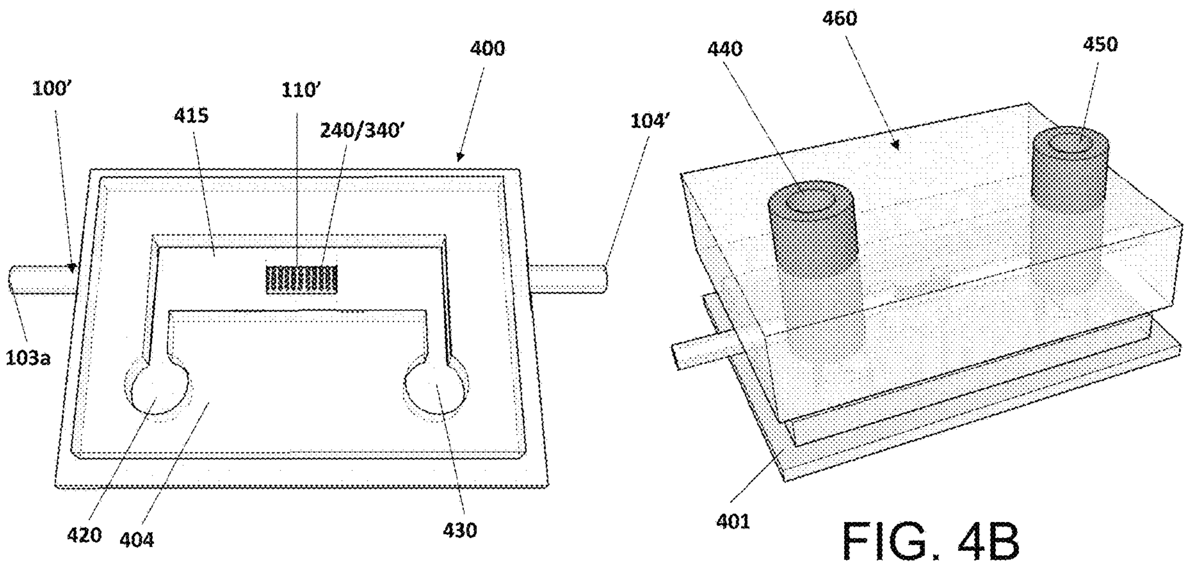
FIG. 4A shows a top-down sectional view of an exemplary fiber-based SERS plasmonic sensor embedded into a microfluidic chip.
FIG. 4B shows an isometric view of the same sensor with a lid featuring inlets and outlets positioned over atop the structure shown in FIG. 4A.
Figure 4C:
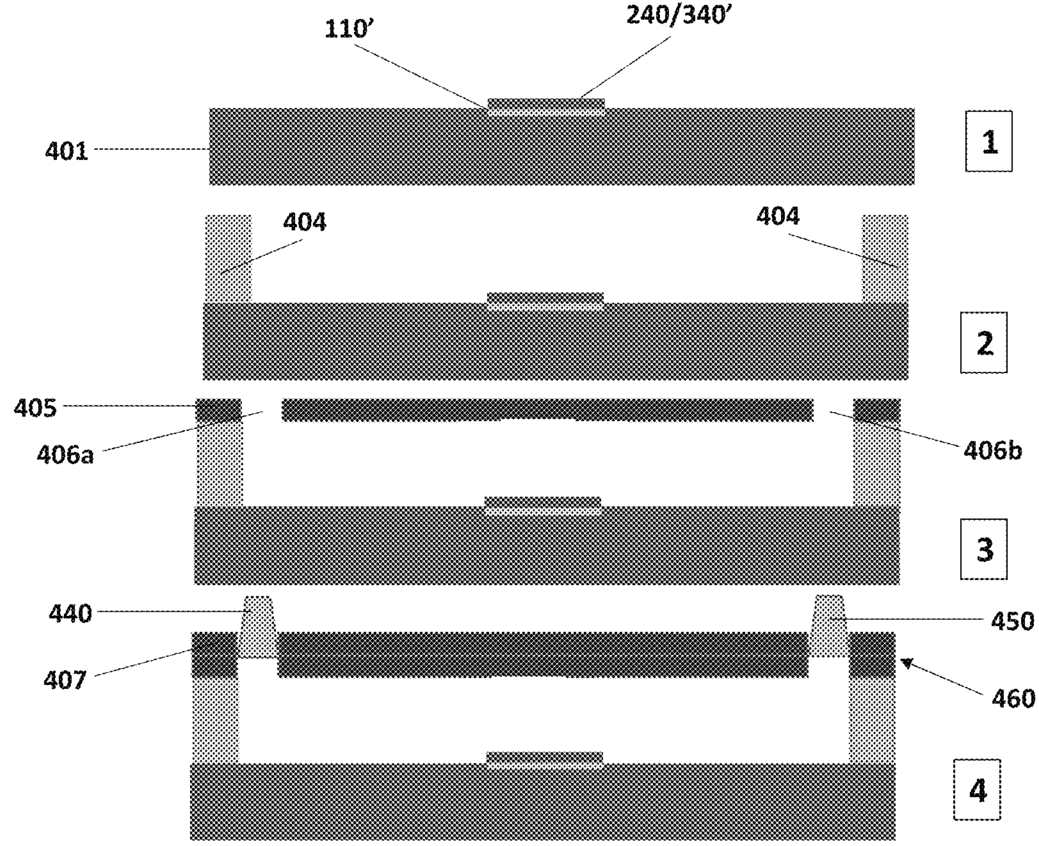
FIG. 4C provides a sequence of cross-sectional view depicting steps for fabricating the exemplary fiber-based SERS plasmonic sensor embedded into a microfluidic chip of FIG. 4A.

Now referring to FIGS. 4A-4C in various embodiments, the present disclosure provides for the encapsulation of an optical fiber 100' with a metallized nanoantennae array 340' on surface 110' into a microfluidic housing designed for the controlled flow of analyte. FIGS. 4A and 4B depict exemplary embodiments of a SERS sensor 400 similar to the SERS sensor 10 described and illustrated above with regard to FIGS. 2A-2F but embedded in a microfluidic chip. The "microfluidic" nature of the device permits more controlled use of small liquid samples volumes and fine control over their flow. The microfluidic chip-based sensor 400 in this exemplary embodiment comprises a foundation 401, a patterned layer 404, a fluidic connector 460 with inlet passage 440 and outlet passage 450, and an optical fiber 100' which has had a longitudinal side region polished to create an exposed-core surface 110' similarly as described above with regard to FIGS. 1A-C. The patterned layer 404 defines a hollow space comprising flow channel 415, an inlet pool 420, and an outlet pool 430. The flow channel 415 connects the inlet pool 420 and the outlet pool 430. As exemplarily illustrated in FIG. 4B, the fluidic connector 460 rests atop the microfluidic chip and comprises the inlet passage 440 and the outlet passage 450, each of which are tubes sized and disposed to fluidly connect with the inlet pool 420 and outlet pool 430, respectively. The surface 110' has a metallized nanoantennae array 340' for SERS sensing as described above with regard to FIGS. 1A-3B, but the optical fiber 100' is not embedded in the support base, such as support base 200 described above. Instead, the optical fiber 100' is embedded in the patterned layer 404.

An exemplary method for construction of the microfluidic chip-embedded SERS sensor of FIGS. 4A-4B is depicted in FIG. 4C. Turning to box 1, fabrication begins with a foundation 401, which in this exemplary embodiment is a glass slide. The foundation 401 is a support block in which an optical fiber 100' is embedded (not shown) as in the exemplary depiction of FIG. 1 and FIGS. 2A-2F. The foundation 401 and optical fiber 100' have been polished to expose a surface 110' on which a metallized nanoantennae array 340' has been prepared as previously described. Turning to box 2, a bulk patterned layer 404 is applied atop the foundation 401. The bulk patterned layer 404 is so patterned as to define the space comprising the inlet pool 420, flow channel 415, and outlet pool 430. In this exemplary embodiment, the bulk patterned layer 404 is a layer of photoresist with a thickness of 125-150 μm which, after application, is cured at cured at a predetermined temperature, e.g., 150° C. Use of photoresist as the material for the bulk patterned layer 404 allows for ease of patterning, since a mask in the shape of the intended layer, UV light exposure, and photoresist developer can be used to pattern the photoresist as described previously. Turning to box 3, a patterned first covering slab 405 is applied atop the bulk patterned layer 404. The first covering slab 405 comprises holes 406*a,b* that are positioned such that when the first covering slap is correctly aligned atop the bulk patterned layer 404, the holes **406*a* and 406*b* are above the inlet pool 420 and outlet pool 430, respectively. In this exemplary embodiment, the first covering slab 405 is made of PDMS that has been mixed with a curing agent and loaded into a 3D-printed mold, then cured overnight, exposed to oxygen plasma, and heated to 100° C. for 20 minutes. In this exemplary embodiment, the first covering slab 405 is bonded to the bulk layer 404 at 50° C. with adhesive and the aid of oxygen plasma. Oxygen plasma is used because it causes exposed surfaces to become more hydrophilic, making application of the adhesive easier. In this exemplary embodiment, a patterned second covering slab 407, shaped and disposed to overlap with and complement the first covering slab 405, comprises inlet passage 440 and outlet passage 450. The second covering slab 407 is adhered to the first covering slab 405 with the aid of an adhesive layer and oxygen plasma. Together, the first 405 and second 407 covering slabs as well as the inlet 440 and outlet 450 passages make up the fluidic connector 460**.

Alternatively, the fluidic connector 460 can comprise only a single covering slab. In this case, the inlet passage 440 and outlet passage 450 are placed in holes **406*a* and 406*b***, respectively.

The binding of the fluidic connector 460 to the bulk layer 404 can be further reinforced with known cross-linking agents as well as additional adhesive such as epoxy glue.

The use and operation of the microfluidic SERS sensor 400 embodiment as exemplarily illustrated in FIGS. 4A-4C is as follows. A liquid sample solution containing biological or chemical specimens of interest enters into inlet passage 440 and proceeds from there into inlet pool 420. From there, the sample solution flows into the flow channel 415, where it passes over the metallized nanoantennae array 340' formed or deposited on the exposed polished surface 110' of the optical fiber 100'. The sample solution continues to flow, eventually passing into the outlet pool 430 and out the outlet passage 450. When the sample solution is passing over the metallized nanoantennae array 340', biological and chemical specimens of interest can contact and adsorb onto the metallized nanoantennae array 340'. As described in the use and operation of the first embodiment disclosed above, these specimens of interest are detected by passaging laser light through the optical fiber 100' to interact with the specimens of interest and thereby generate Raman signals which are enhanced by the metallized nanoantennae array 340. These signals travel toward a first end 103'. From here, the signals are, as exemplarily illustrated in FIG. 1A-B, collected by a detector **119*a***, at which point they can be processed.

Although the SERS sensor 400 embedded in a microfluidic chip as depicted in the exemplary embodiment FIGS. 4A-4C is shown to comprise particular features of specific dimensions and material compositions, one of ordinary skill in the art could readily envision variations that are considered to be within the scope of the present disclosure. For example, in one or more alternative embodiments, the optical fiber can comprise more than one polished surface 110' with metallized nanoantennae array 340'. The flow channel 415, rather than being a straight passage, can incorporate features to slow or redirect flow, such as a variation of a serpentine channel, for example.

An alternative embodiment can incorporate more than one outlet pool 430 and outlet passage 450. In an alternative embodiment, the fluidic connector 460 can be comprised of only a single covering slab that incorporates the inlet and outlet passages. Although the exemplary embodiment of FIGS. 4A-4C is described as using glass, PDMS, and photoresist as materials for the microfluidic chip housing 410, other materials that satisfy the strength and rigidity requirements of the microfluidic chip's construction are considered to be within the scope of the present disclosure. An alternative embodiment can have the optical fiber lay orthogonal to the flow path, or at an angle thereto, while keeping the nanoantennae array 340 within the flow path.

Referring now to FIGS. 5A, 5B and 6A-6C, a more advanced sensor 500 with an embedded optical fiber featuring a metallized nanoantennae array for SERS formed and deposed on a polished surface on a longitudinal side surface 110" of an optical fiber 100" will now be described. This more advanced microfluidic sensor contains focusing and trapping functionality. The focusing functionality enables the sensor 500 to further concentrate dilute sample solutions by applying electric fields that guide the flow of biological and chemical specimens of interest. The trapping functionality enables the sensor 500 to slow the flow of such specimens while they are passing over the metallized nanoantennae array 340", thus increasing the likelihood that such specimens will contact and adsorb onto the array 340" and thereby be detected.

Figure 5A:
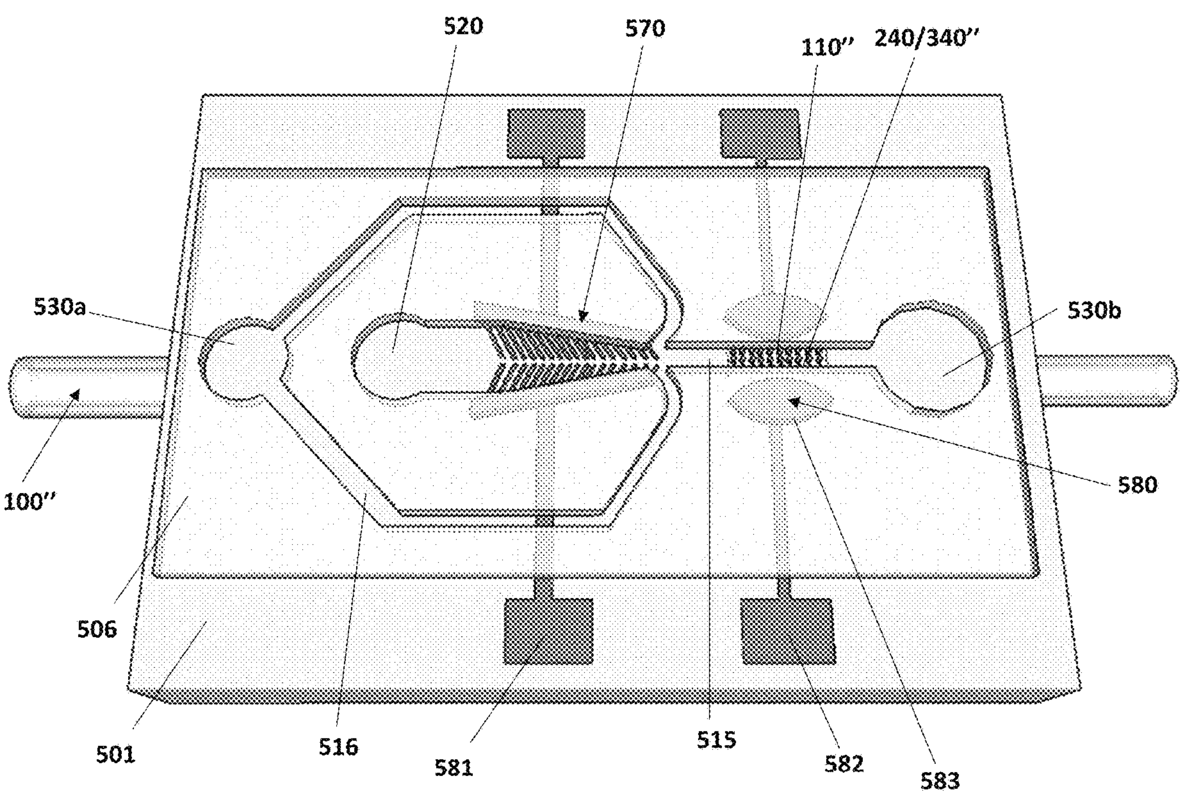
FIGS. 5A-5B show a complete exemplary depiction of a plasmonic sensor with a single focusing region and a trapping region.
Figure 5B:
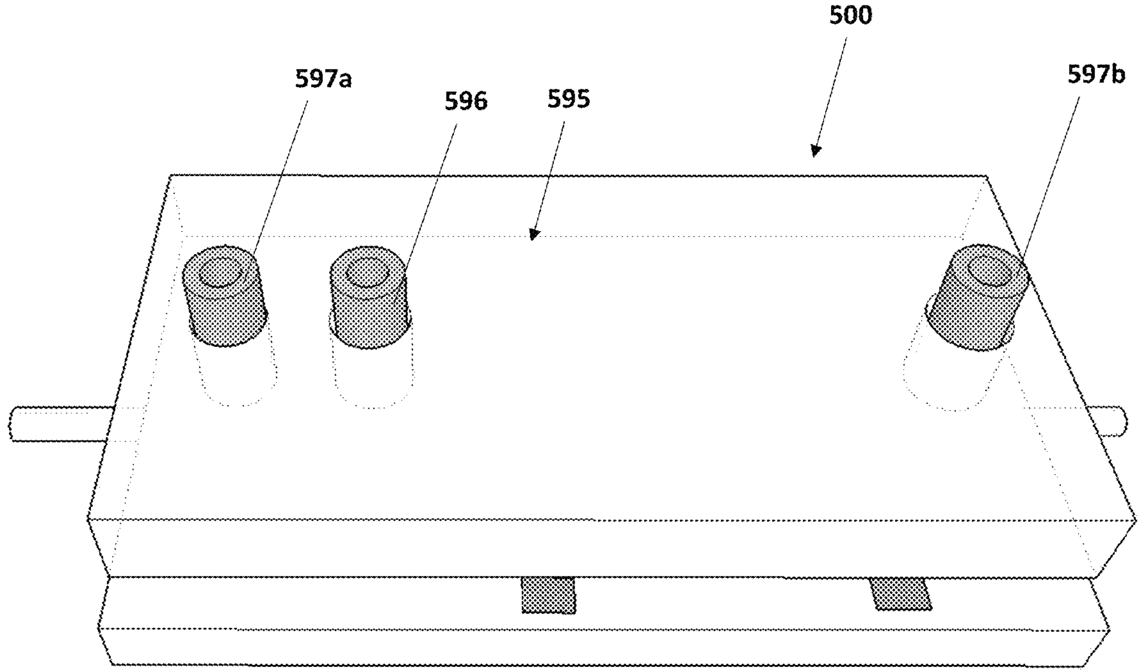
Figures 6A, 6B, 6C:
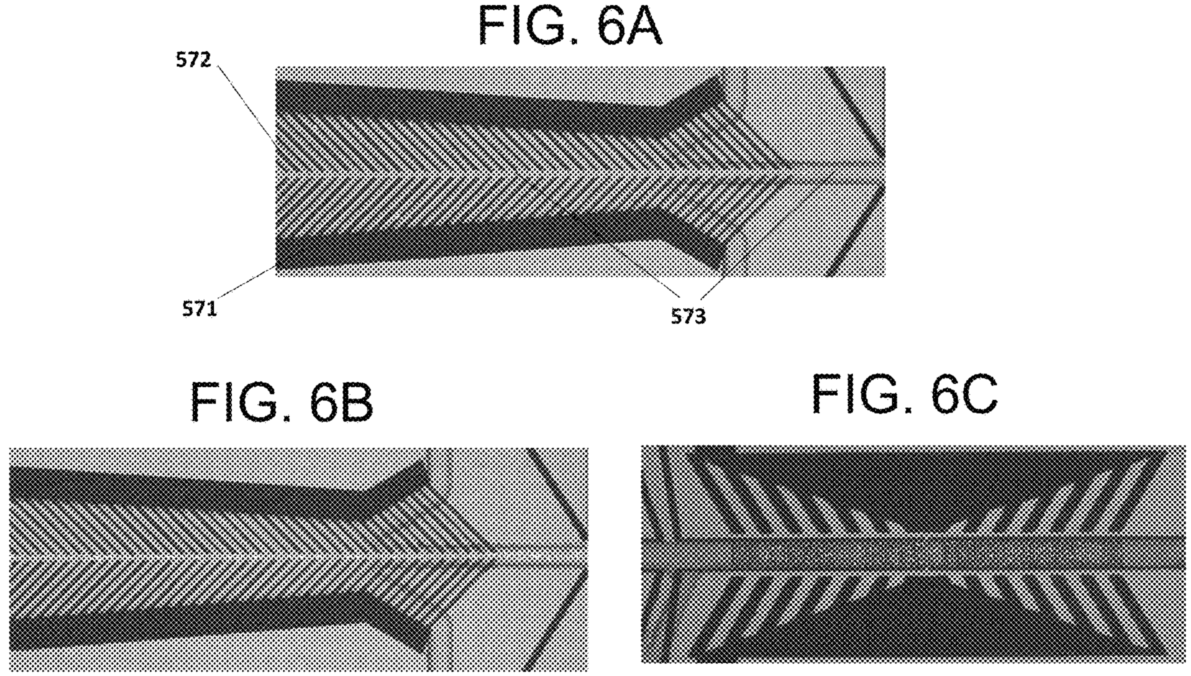
FIGS. 6A and 6B show comparative images of focusing regions with focusing turned 'off' and 'on,' respectively.
FIG. 6C shows an image of a trapping region with analyte particles trapped.

Turning first to FIGS. 5A-5B, a microfluidic chip 500 with focusing functionality comprises an optical fiber 100" featuring a polished surface 110" and metallized nanoantennae array 340" formed on a longitudinal side of the optical fiber 100", a base 501, a patterned bulk layer 506, focusing regions 570, trapping regions 580, focusing leads 581, trapping leads 582, and a fluidic connector 595. This microfluidic chip is an improvement of a design previously presented in U.S. Pat. No. 10,274,492 which is incorporated herein by reference in its entirety. The bulk patterned layer 506 defines a hollow space that comprises an inlet pool 520, outlet pools **530*a* and 530*b*, a primary flow channel 515, and waste flow channels 516. The focusing region 570 is shown in more detail in the exemplary embodiment shown in FIGS. 6A-6B. The focusing region 570 comprises plated vertical sidewalls 571, thin film fingers 572, and dielectrophoretic (DEP) region 573. The fluidic connector 595 comprises an inlet passage 596 and outlet passages 597*a* and 597*b*. The trapping regions 580 are shown in more detail in the exemplary embodiments shown in FIGS. 7B and 7C. The trapping regions 580 each comprise a trapping electrode 583 and, in at least one exemplary embodiment, finger-like extensions 584**.

Figures 7A, 7B, 7C:
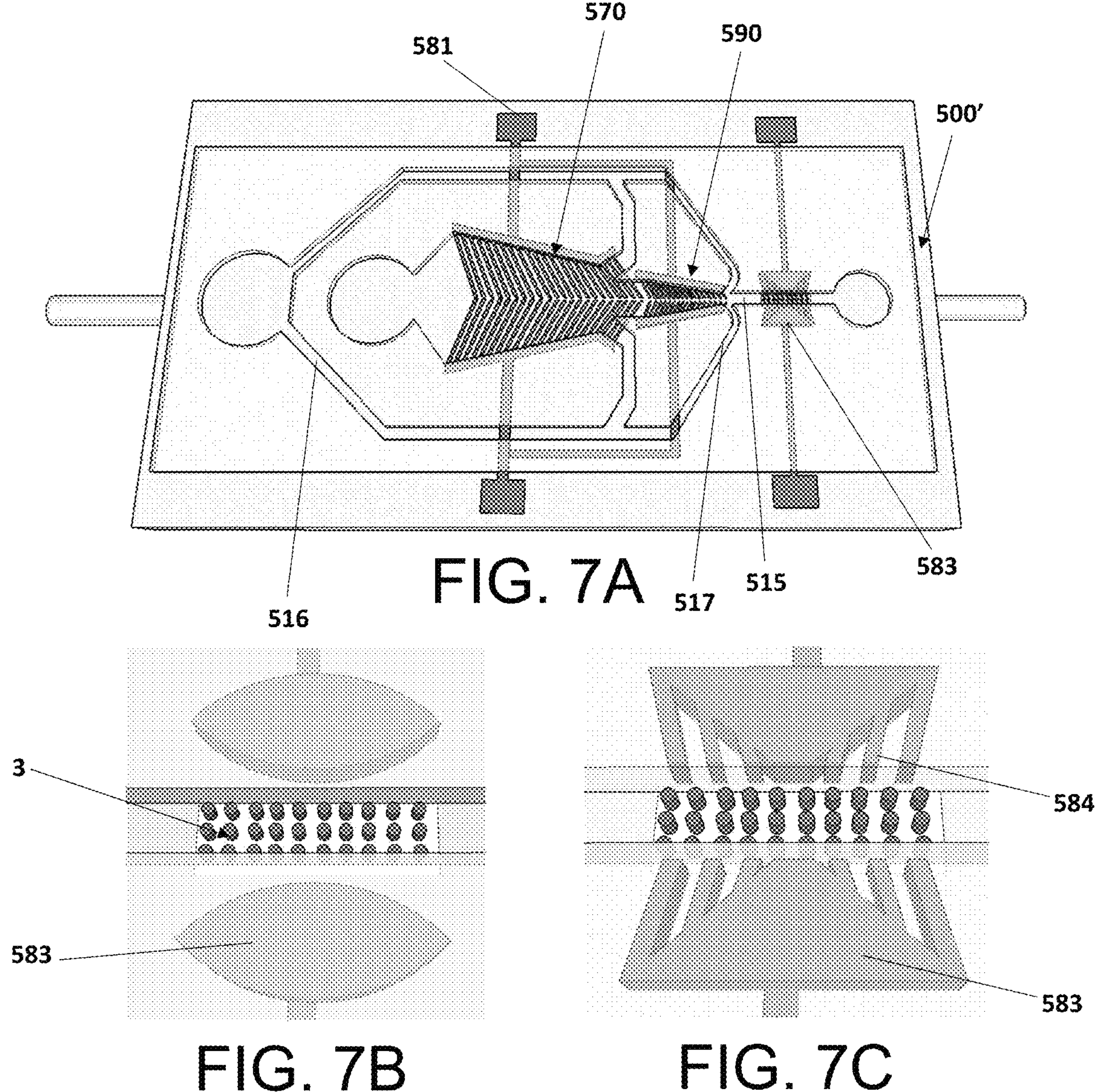
FIG. 7A shows an alternative exemplary depiction of a plasmonic sensor as in FIGS. 5A-B but with two focusing regions and an alternative trapping region.
FIGS. 7B and 7C are comparative depictions of different trapping region designs.

An alternative exemplary embodiment of the more enhanced microfluidic chamber with embedded SERS sensor 500' is shown in FIG. 7A, which further comprises a second focusing region 590 positioned just after the focusing region 570 along the flow channel 515, as well as an auxiliary waste line 517 positioned after the second focusing region. This exemplary embodiment also features a distinct trapping electrode design. Comparison of two trapping electrode 583 designs can be seen in FIGS. 7B and 7C. FIG. 7B shows a substantially elliptical trapping electrode, while FIG. 7C shows a substantially triangular trapping electrode with finger-like extensions 584.

An exemplary method for construction of an advanced microfluidic chamber with embedded SERS sensor, one or more focusing regions, one or more trapping electrodes, a flow channel and one or more waste lines is provided in FIGS. 8A-8F. First, the base 501 comprising an optical fiber 100" that has had its longitudinal side 110" polished and coated with a metallized nanoantennae array 340" is coated with a foundation layer 502. This foundation layer 502 helps to ensure that the base 501 better adheres to subsequently applied materials and can be applied atop the metallized nanoantennae array 340" without harming it.

Figures 8A, 8B:
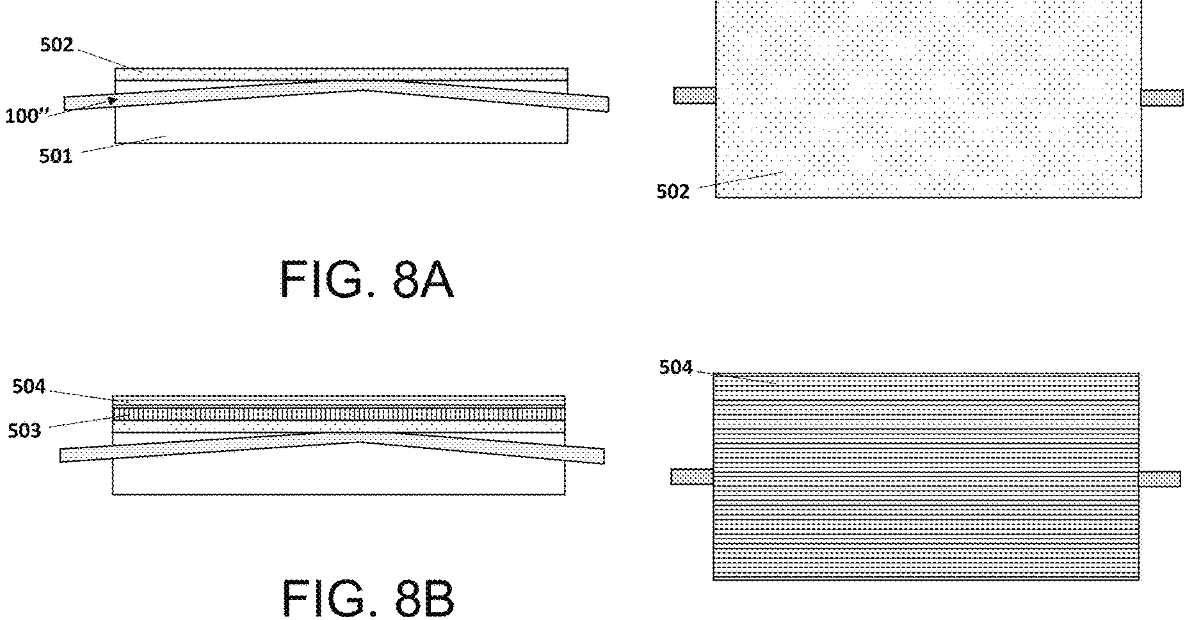
FIGS. 8A-8F provide an exemplary depiction of a sequence of steps for fabricating an embodiment of a plasmonic sensor that incorporates the patterned longitudinal side of a fiber optic embedded in a support platform that comprises a focusing region, confinement electrodes, an inlet pool, outlet pools, and waste channels.
Figures 8C, 8D:
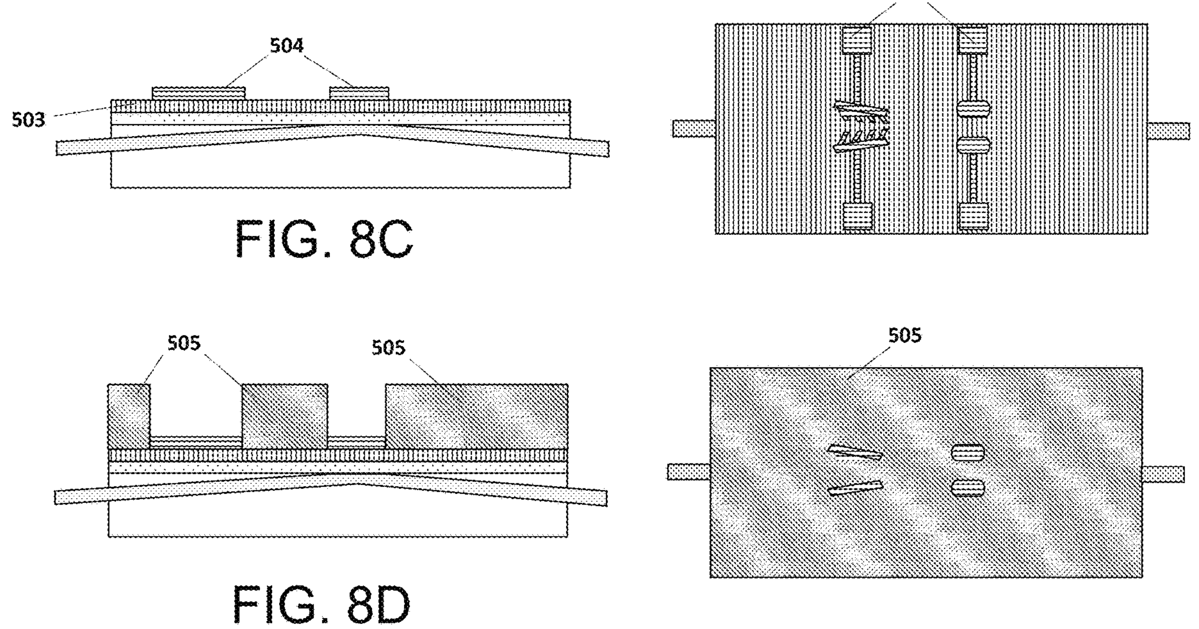

In the exemplary embodiment of FIGS. 8A-8F, the base 501 is a 3D printed mold and the foundation layer is a photoresist. Turning to FIG. 8B, an adhesion layer 503 is applied atop the foundation layer 502, followed by a seed layer 504. The adhesion layer 503 is intended to help the seed layer 504 to adhere to the foundation layer 502. Both the adhesion layer 503 and the seed layer 504 are typically conductive, and the seed layer is deposited for creating the focusing and trapping electrodes. In this exemplary depiction, the adhesion layer 503 is a coating of approximately 10 nm thick chromium, while the seed layer 504 is a coating of 30 nm thick gold. The seed layer serves as a base from which parts of the focusing regions and trapping regions will be shaped and grown. Thus, and as seen in FIG. 8C, the seed layer is subsequently etched to achieve the desired underlying pattern for electrode structures. In this exemplary embodiment, wet etching achieves the desired result, but a variety of dry etching techniques could also work. Although no wet etching protocol is shown here, the technique is well-established and many variations on the approach are known to one of ordinary skill in the art. As FIG. 8D shows, this step is followed by casting a patterned layer of an electroplating mask 505. The electroplating mask 505 is applied and patterned so that the only regions not covered by the electroplating mask are the regions of the etched seed layer 504 that will become the focusing region's vertical plated side walls 571 and the trapping electrodes 583. Thus, these unmasked regions are the only conductive regions that will grow when electroplated. In this exemplary embodiment, the electroplating mask 505 is AZ P4620 photoresist, which is relatively easy to pattern for reasons discussed earlier.

Figures 8E, 8F:
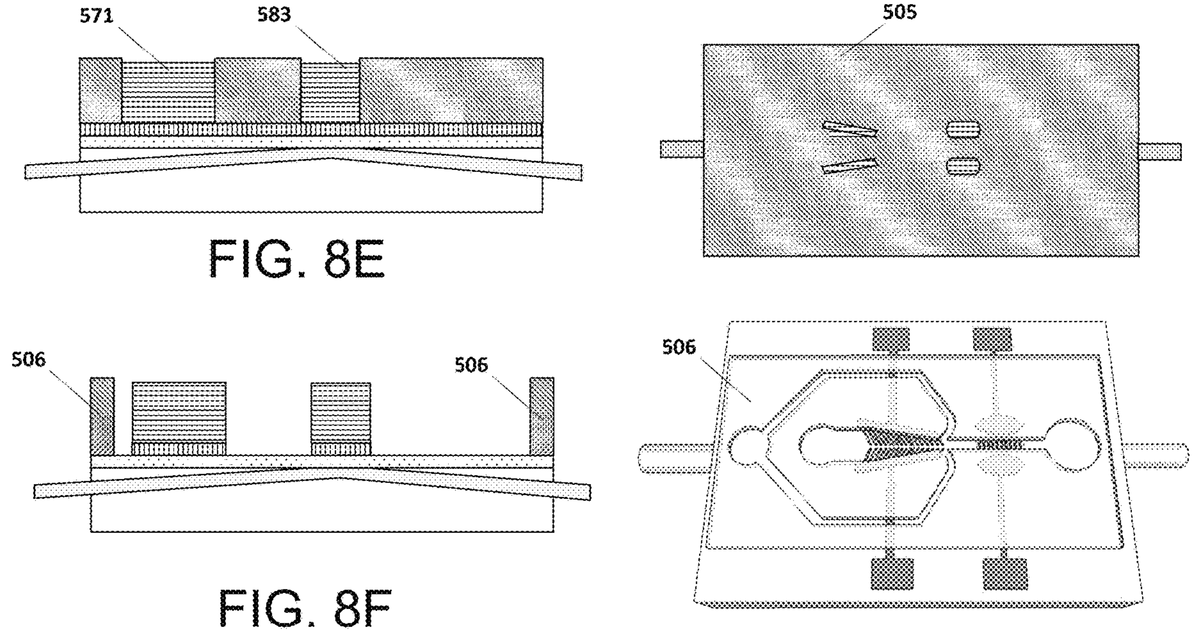

A depiction of the subsequent formation of the vertical side walls of the focusing electrode(s) 571 and the trapping electrodes 583 by electroplating is provided in FIG. 8E. The sections of etched seed layer 504 not covered by the electroplating mask 505 are connected to a power supply which is also connected to a counter electrode. Electroplating proceeds as described previously. After this point, the electroplating mask 505 is removed by any of the known means previously discussed, including peeling, washing, or ashing, and the exposed regions of adhesion layer 504 are also removed by any appropriate means known in the art, including wet and dry etching. Although many options are known to one of ordinary skill for growing these electrodes, including lift off and thin film deposition processes, and are furthermore considered to be within the scope of this disclosure, electroplating was here found to be particularly successful.

Then, as shown in the exemplary depiction of FIG. 8F, the patterned bulk layer 506 is deposited and patterned, thereby defining the hollow space comprising the inlet pool 520, outlet pools 530*a* and *b*, flow channel 515, and waste channels 516 and optionally 517. In this exemplary embodiment, the bulk layer 506 is SU 8 2025 photoresist, with photoresist being used due to its ease of patterning, as discussed previously.

The fluidic connector 595 is then applied on top of the patterned bulk layer 506 to complete the sensor embodiment 500 as shown in FIG. 5B by means discussed previously with respect to the microfluidic cell embodiment 400 and depicted in FIG. 4C. Any adhesive means known to those of skill in the art are within the scope of the present disclosure.

During operation, a sample solution containing a biological or chemical specimen of interest enters into the inlet pool 520 and flows across the focusing region 570. The focusing leads 581 can be connected to a power supply to apply an AC voltage across opposing thin film fingers 572 of the focusing region, where resultant dielectrophoretic forces focus the flow of analyte along the dielectrophoretic region 573 toward the array 340. This focusing effect can be seen clearly by comparing FIGS. 6A and 6B, where the white dots are polystyrene beads with sub-micron diameters that represent the biological or chemical specimen of interest that, in FIG. 6B, has been corralled into the region between opposing thin film fingers 572. In various exemplary embodiments, focusing was performed by applying an alternating current (AC) voltage of 4V peak-to-peak at 5 megahertz (MHz). Any excess solution that is left over after the specimen of interest is concentrated in the focusing region 570 flows instead along waste flow channels 516 and toward outlet pool 530*a*. Solution containing concentrated analyte flows through channel 515 over the enhanced surface 110. The trapping leads 582 can be connected to a power supply to apply an AC voltage across opposed trapping electrodes 583. There, an electric field from the trapping electrodes 583 slows the specimen's flow over the enhanced surface 110. In various exemplary embodiments, trapping was performed by applying an AC voltage of 5V peak-to-peak at 6 MHz. SERS detection can occur as described earlier and in FIG. 1, and from there, the concentrated sample solution flows to outlet pool 530*b*.

The exemplary embodiment shown in FIGS. 7A-7C has additional focusing and trapping functionality. By keeping waste line 516 to divert flow of excess solvent after the first focusing region 570 and having auxiliary waste line 517 to divert flow of excess solvent after the second focusing region 590, the analyte solution effectively undergoes multiple rounds of analyte concentration prior to reaching the SERS detector array 340. The finger-like extensions 584 seen appended to the trapping electrode 583 in FIG. 7C shape the applied electric field to retain specimens of interest for longer over the SERS sensing array 340.

Figure 10A:
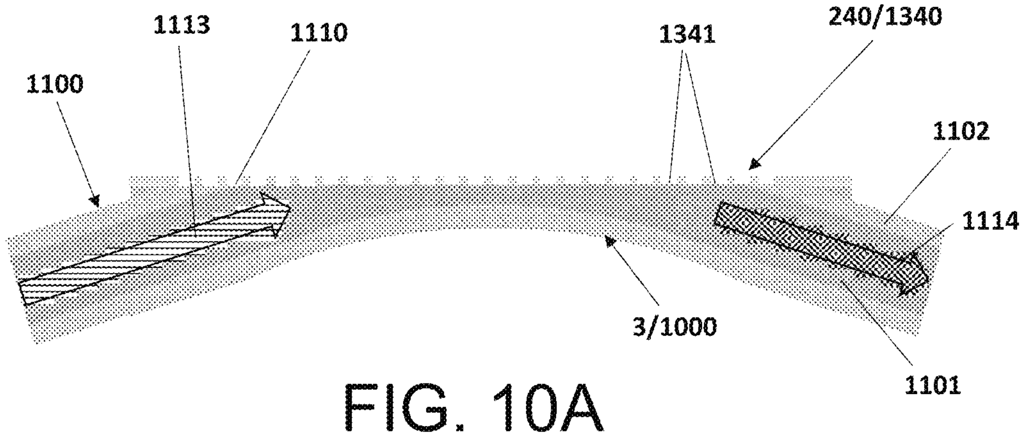
FIGS. 10A and 10B exemplarily illustrate the optical fiber-based plasmonic sensor system shown in FIG. 1, comprising an exemplary plasmonic RI sensor fabricated on the longitudinal side of an optical fiber embedded in a support base, in accordance with various embodiments of the present disclosure.

Turning now to FIG. 10A, alternatively to the implementation of SERS, the plasmonic sensors 3/10 of the embodiments described above can incorporate RI sensing functionality in lieu of SERS sensing functionality. For example, in various embodiments the plasmonic sensor 3 can comprise an RI sensor 1000 as shown in FIG. 10A formed on an optical fiber 1100. The optical fiber comprises a core 1101 and a cladding 1102. A section of the core 1101 is exposed to reveal a polished longitudinal side surface 1110 on which a metallized nanoantennae array 1340 is deposited. The metallized nanoantennae array 1340 comprises a pattern of individual nanoantennae, which in various embodiments comprises a plurality of nano sized holes 1341 that terminate at the top surface 1110.

Figures 11A, 11B, 11C, 11D:
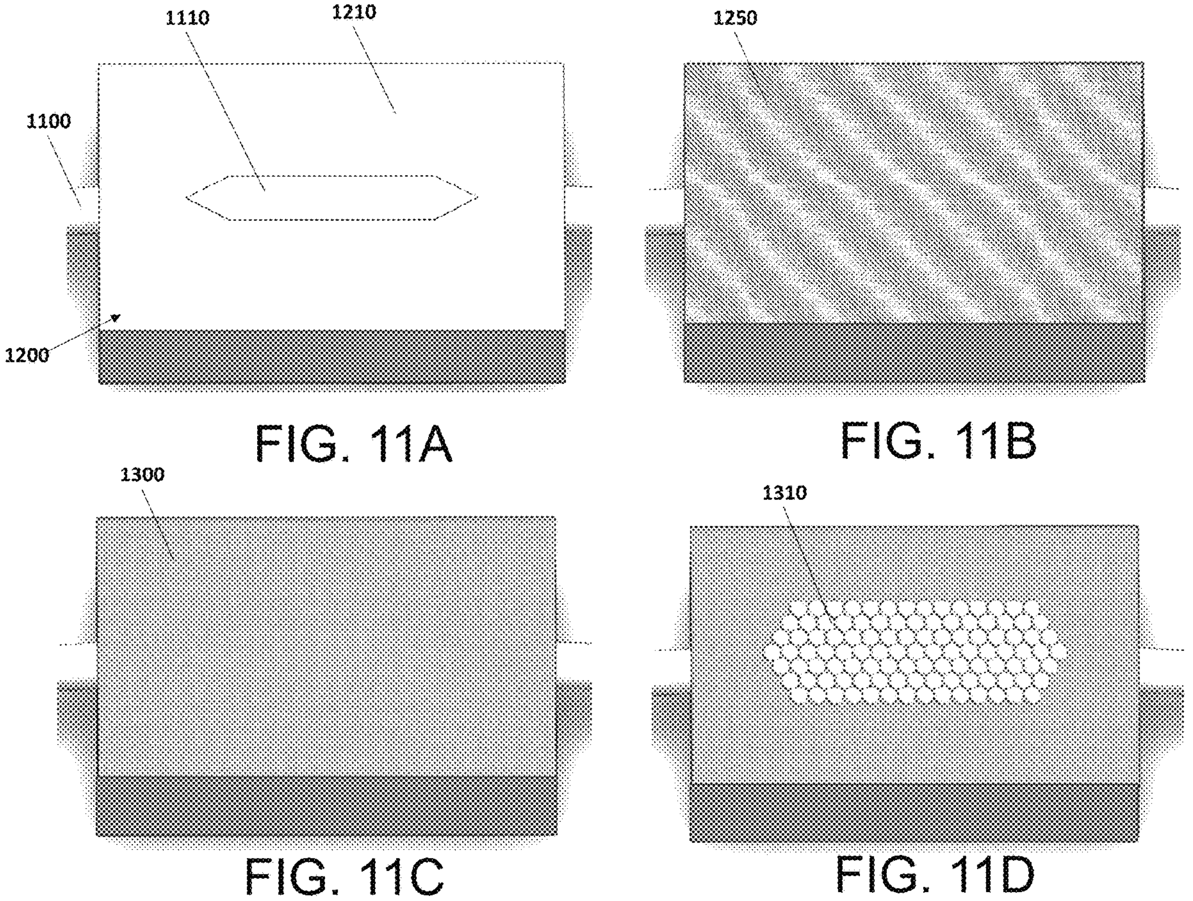
FIGS. 11A-11H provide a depiction of an exemplary sequence of steps for fabricating an RI plasmonic sensor on the longitudinal side of an optical fiber that is embedded in a support platform, such as that shown in FIG. 10A, jn accordance with various embodiments of the present disclosure.

An exemplary fabrication method for the RI sensor 1000 is shown in FIGS. 11A-11G. First, and as seen in FIG. 11A, an optical fiber 1100 is embedded in a support base 1200 with an upper surface 1210, and this upper surface is abraded until a section of the fiber optic core is exposed as the longitudinal side surface 1110. As seen in FIG. 11B, a nanoantennae layer 1250 is then deposited on the coplanar side surface 1110 and surface 1210 by sputtering, chemical vapor deposition, or any other means known in the art. In various embodiments, the nanoantennae layer 1250 is a layer of aluminum between 1 and 500 nm thick, for example 50 nm thick, however it can also be made of any conductive material known to one of skill in the art. The nanoantennae layer provides the basis for the eventual formation of a metallized nanoantennae array 1340 (e.g., the plurality of nano sized holes 1341 that terminate at the top surface 1110).

Then, as seen in FIG. 11C, a photoresist layer 1300 is applied atop the nanoantennae layer 1250 to a thickness that in various embodiments can be between 50 nm and 10 μm, for example 400 nm. The purpose of the photoresist layer 1300 is to provide a mask for etching the nanoantennae layer 1250 to generate a metallized nanoantennae array 1340 comprising holes (e.g., RI embodiments) rather than discs (e.g., SERS embodiments). Microsphere lithography is then performed as described previously, by depositing a self-assembling layer of microspheres 1310 and irradiating them with UV light to produce a regular pattern of holes 1320 that extend down to an uppermost surface of the nanoantennae layer 1250, as seen in FIGS. 11D and 11E. The exposed portions of the nanoantennae layer 1250 are then etched by wet chemical etching or any other means known to those in the art, generating deeper holes 1321 that extend through both the photoresist layer 1300 and the nanoantennae layer 1250 and terminate on the coplanar side surface 1110 and surface 1210. The photoresist layer 1300 is then removed by any known means known in the art, as discussed previously. What remains, as seen in FIG. 11G, is a metallized nanoantennae array 1340 comprising the array of nano sized holes 1341 that terminate on longitudinal side surface 1110.

Figures 11E, 11F, 11G, 11H:
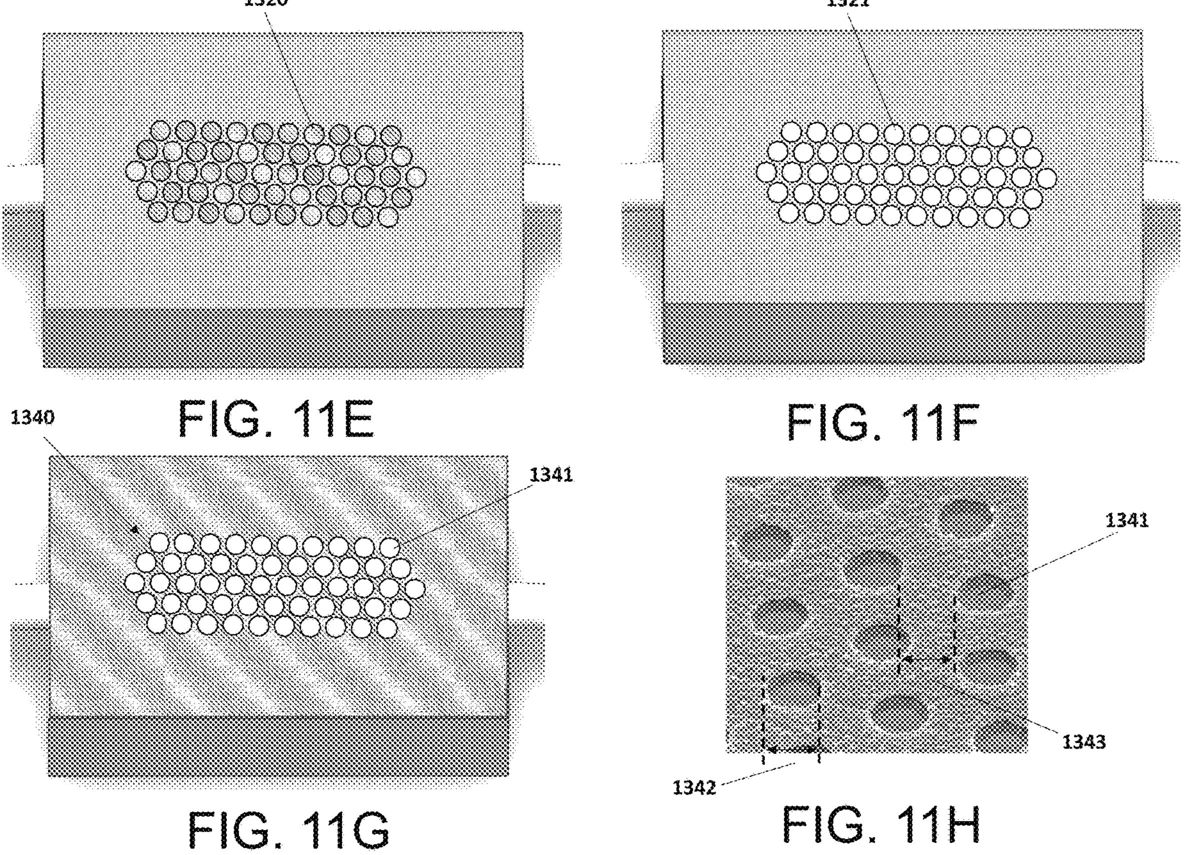

FIG. 11H provides a photograph of an exemplary embodiment of the metallized nanoantennae array 1340 in which can be seen the array of holes 1341 with width 1342 and inter-hole spacing 1343. In various embodiments, and as discussed previously, the size, relative disposition, and composition of the microspheres 1310 can affect the size and relative disposition of the holes 1341, as can the extent and angle of UV light exposure. In various embodiments, the hole width 1342 can range from 100 to 1000 nm, and the inter-hole spacing 1343 can range from 100 nm to 5 μm, and for example be 1 μm.

The above-described RI sensor embodiment 1000 can be employed in place of SERS sensors 10, 400, 500, and 500' described above and exemplarily illustrated in FIGS. 1A-8F in any of the respective embodiments simply by replacing each embodiment's modified optical fiber with the one described and shown with regard to FIG. 10A. For sensor embodiments that do not comprise a support base 1200 or similar structure, the optical fiber 1100 can be removed from the support base after fabrication of the sensor 1000 by physical peeling or elimination of the support base by means known to those of ordinary skill in the art.

Turning again to FIGS. 10A-10B, use of RI sensor embodiments is briefly described. Laser light 1113, provided by a laser source as described earlier with respect to FIGS. 1A-1B, travels through the optical fiber 1100 until it reaches the surface 1110 with metallized nanoantennae array 1340. There, the laser light 1113 resonates with plasmons in the metallized nanoantennae array 1340 in a manner governed by a local refractive index, producing a signal 1114 that can be acquired in the same manner as described previously and with regard to FIGS. 1A-1B. When biological or chemical specimens of interest 1111 come onto or near the metallized nanoantennae array 1340, their presence induces a change in the local refractive index. This in turn shifts the frequency of maximum resonance, generating an altered signal 1115. The altered signal 1115 can be acquired in the same manner as described previously and with regard to FIGS. 1A-1B. By comparing the signal 1114 with the altered signal 1115, a user can determine the presence of specimens of interest 1111.

Figure 12A:
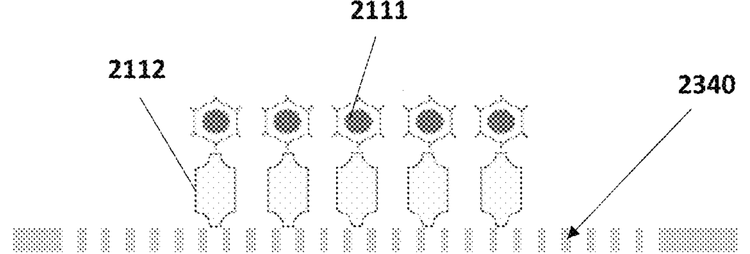
FIG. 12A provides a depiction of an exemplary embodiment of the metallized nanoantennae array that features a detection layer for improving the selectivity of the sensor.

All of the herein described plasmonic sensor embodiments can be further modified to improve their selectivity through the use of a detection layer. Turning to FIG. 12, a metallized nanoantennae array 2340 (e.g., an array of nano sized discs (SERS) or holes (RI) is shown with a detection layer 2112 atop the array. The detection layer 2112 is so composed as to specifically bind to biological and chemical specimens of interest 2111. By binding solely to the specimens of interest 2111, the detection layer 2112 reduces the likelihood that biological or chemical specimens irrelevant to the sensor will not interfere with the generation of a desired signal.

In various exemplary embodiments, the metallized nanoantennae array 2340 can comprise either discs or holes to function for either a SERS or RI plasmonic sensor. In various exemplary embodiments, the detection layer 2112 can comprise antibodies known to selectively bind to specific antigens.

Figure 12B:
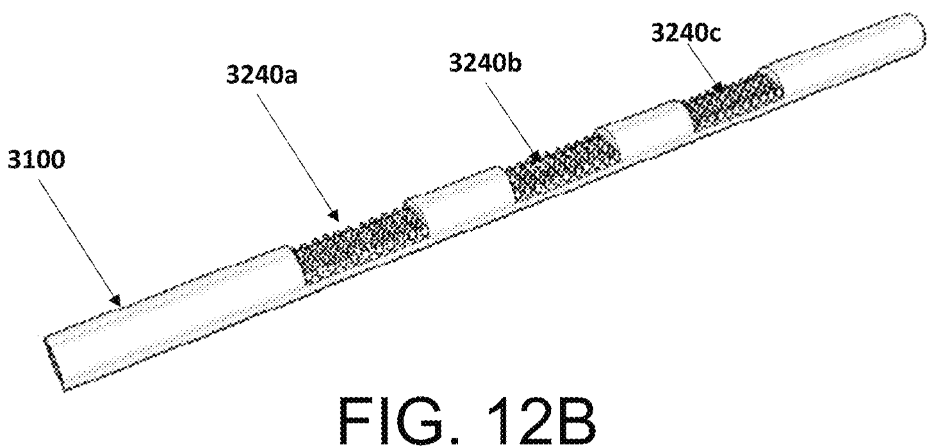
FIG. 12B provides a depiction of an exemplary embodiment of an optical fiber comprising three noncontiguous metallized nanoantennae arrays for increasing the multiplex detection capacities of the sensor.

The herein described plasmonic sensor embodiments can also be further modified to increase their sensing capacity by introducing a plurality of metallized nanoantennae array in a single optical fiber, as shown in FIG. 12B. In the exemplary embodiment of FIG. 12B, three non-contiguous metallized nanoantennae arrays, 3240*a*, 3240*b*, and 3240*c*, are formed on a single optical fiber 3100 via the polishing and fabrication techniques previously discussed, as in FIGS. 2A-2F.

During operation, a first sample containing one or more biological or chemical specimens of interest can be introduced to the metallized nanoantennae array 3240*a* and detection using light can proceed as discussed previously. After detection, the metallized nanoantennae array 3240*a* can be cleaned. In various exemplary embodiments, cleaning of any metallized nanoantennae array can proceed via methods known in the art, for example by rinsing with an appropriate solvent such as deionized water. Then a second sample containing one or more biological or chemical specimens of interest can be introduced to the metallized nanoantennae array 3240*b*. After detection of this sample by means previously discussed, the metallized nanoantennae array 3240*b* can be cleaned and a third sample containing a biological or chemical specimen of interest can be introduced to the metallized nanoantennae array 3240*c* and be detected there.

As an alternative method of use, the metallized nanoantennae arrays 3240*a*-3240*c* may be fabricated specifically for RI sensing, whereby different samples can near-simultaneously undergo detection. In such a case, if a first, second, and third sample are loaded onto metallized nanoantennae arrays 3240*a*, 3240*b*, and 3240*c*, respectively, then the biological or chemical specimens of interest within those samples can undergo near-simultaneous detection by controlling a time delay of light introduced to the optical fiber 3100. By tuning the time delay of the light entering into the optical fiber 3100, one can induce plasmonic resonance first on nanoantennae array 3240*a*, then on array 3240*b*, then on array 3240*c*, without having to wash the nanoantennae arrays during this process.

Although the exemplary embodiment shown in FIG. 12B contains three independent metallized nanoantennae arrays as sensing regions, alternative embodiments can include any non-zero integer number of such metallized nanoantennae arrays, limited only by one's capacity to produce them. Generating a plurality of distinct sensing regions on a single optical fiber can further enhance the multiplex sensing capacity of the sensor while retaining its low cost of production and ease of use.

SPECIFIC EXAMPLES

SERS Sampling of R6G Dye

In order to test the capacity of the disclosed SERS sensing technology to detect specimens of interest at low concentrations, a SERS sensor 10 was fabricated on the longitudinal side of an optical fiber embedded in a support mount, as in the first described embodiment above, and tested using a dye as a liquid sample. In this fabrication, the diameters 345 of the discs 341 in the metallized nanoantennae array 340 were less than 1 μm. The dye selected was Rhodamine 6G (R6G), a red fluorescent dye that produces a spectrum with several distinct characteristic peaks when studied with Raman spectroscopy. Nine solutions of R6G were prepared, each ten times more dilute than the previous, starting at a concentration of $10^{-1}$ molar (M) and ending at $10^{-9}$ M. The patterned SERS sensor 10 was soaked in one solution at a time for several minutes prior to introducing laser light 113 and acquiring a SERS spectrum of the R6G dye. Comparative results can be seen in FIG. 9A. These spectra have been processed to remove background the background spectrum generated by the bare fiber. Only spectra corresponding to the five most-dilute dye solutions are shown and are numbered 1-5. Spectrum 1 corresponds to an R6G solution at a concentration of $10^{-5}$ M; spectrum 2 corresponds to a solution at a concentration of $10^{-6}$ M; spectrum 3 corresponds to a solution at a concentration of $10^{-7}$ M; spectrum 4 corresponds to a solution at a concentration of $10^{-8}$ M; spectrum 5 corresponds to a solution at a concentration of $10^{-9}$ M. Spectral peaks that are characteristic of R6G dye have been marked with vertical dashed lines that are labeled A-E. Peak A is centered at approximately 1033 $cm^{-1}$; peak B is centered at approximately 1205 $cm^{-1}$; peak C is centered at approximately 1315 $cm^{-1}$; peak D is centered at approximately 1380 $cm^{-1}$; peak E is centered at approximately 1531 $cm^{-1}$. All characteristic peaks are still clearly observable in spectrum 5, while some, such as peak B, are still clearly present in spectrum 5. Thus, the detection limit for this simple embodiment is approximately $10^{-9}$ M. However, further amplification is known to be possible through a few means, including increasing the surface area of the exposed optical fiber surface 110, increasing the average diameter of discs 341, and patterning the nanoantennae array 340 into 'clusters' of multiple discs.

Figures 9A, 9B:
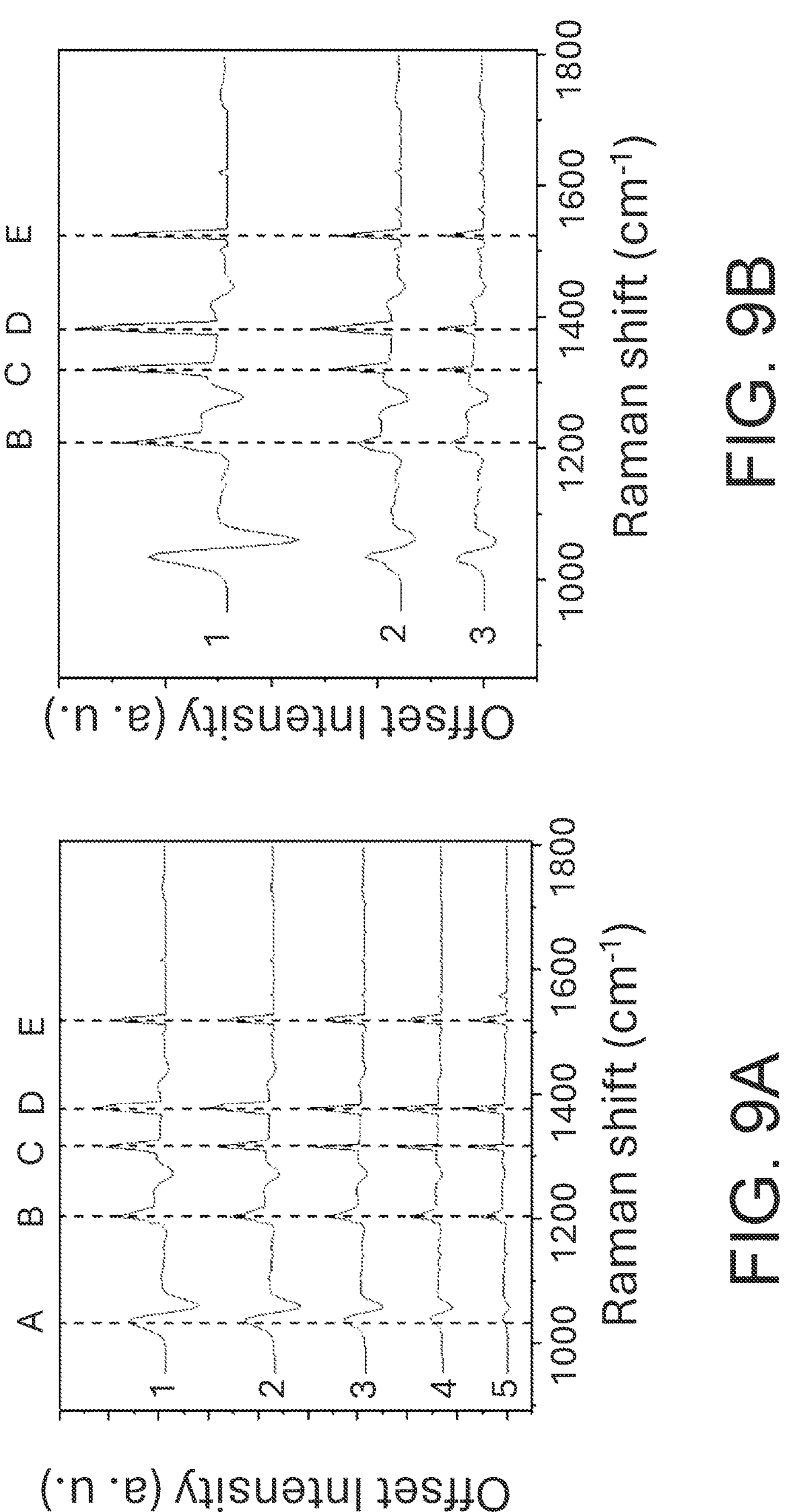
FIG. 9A provides comparative spectra of SERS signals taken from dye samples of decreasing concentrations using the disclosed SERS sensor.
FIG. 9B shows comparative spectra of SERS signals taken with a constant dye sample concentration but varying metallized disc diameters on the sensing region.

To demonstrate the potential for these signal enhancement effects, SERS sensors of the present disclosure were fabricated with metallized nanoantennae arrays 340 whose disc diameters 345 varied, with all other variables being kept constant. In order to assess the relative sensitivities of these variations in sensor fabrication, they were exposed to a solution of R6G dye of fixed concentration of $10^{-5}$ M for several minutes, after which point laser light 113 was applied as in FIG. 1A and SERS spectra were collected. Comparative spectra for this study are shown in FIG. 9B, with each spectrum labeled 1-3. Spectrum 1 corresponds to a sensor with an optical fiber diameter 115 of 4 mm and disc diameters 345 of 800 nm. Spectrum 2 corresponds to a sensor with an optical fiber diameter 115 of 2 mm and disc diameters 345 of 800 nm. Spectrum 3 corresponds to a sensor with an optical fiber diameter 115 of 2 mm and disc diameters 345 of 600 nm. As can be seen, the intensity of characteristic R6G spectrum peaks B-E increases dramatically with increased with increasing fiber diameter 115 as well as disc diameters.

Figure 10B:
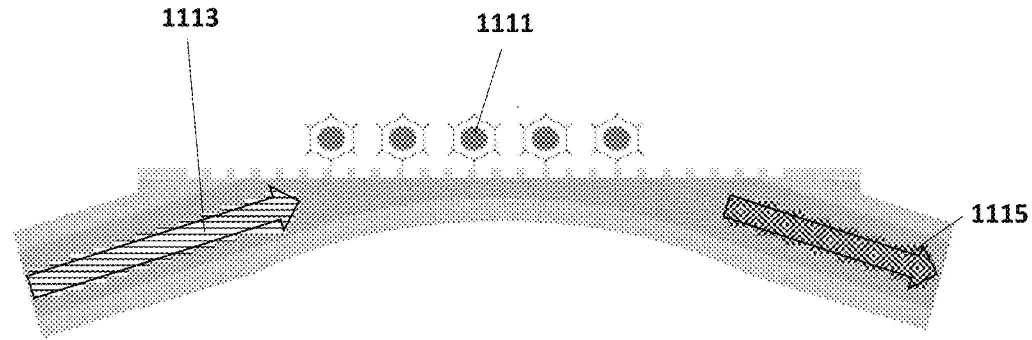

Finally, the strategic clustering of discs 341 in the metallized nanoantennae array 340 was studied by fabricating optical fiber-based SERS sensors of the present disclosure featuring metallized nanoantennae array patterns like that seen in FIG. 10B. The exemplary pattern of FIG. 10B was fabricated using microsphere lithography by deliberately altering the angle of incidence and exposure time of UV light, producing an array of four-disc clusters. Alterations in the composition of these clusters can also influence the sensitivity of a detector. This was demonstrated by producing another optical fiber-based SERS sensor of the present disclosure, tailoring the microsphere lithography of its fabrication so that its metallized nanoantennae array 340 would feature three-disc clusters. The four-disc and three-disc cluster SERS sensors were then tested by immersing them for several minutes in an R6G solution of fixed concentration. The resulting spectra are shown in FIG. 10A. Spectrum '1' corresponds to the SERS sensor with an array of 4-disc clusters, while '2' corresponds to two overlapping spectra of the SERS sensor with an array of 3-disc clusters. Spectrum 1 clearly has improved signal strength and a higher signal-to-noise ratio, indicating that the advanced roughness of the four-disc cluster is more advantageous.

In view of the above, it will be seen that the several objects and advantages of the present invention have been achieved and other advantageous results have been obtained. The SERS sensor of the present disclosure provides for single or multiplex detection of a vast variety of chemical and biological specimens, has a signal output further enhanced by patterning the larger surface area of the longitudinal side of an optical fiber, and has a simple, low-cost methods of fabrication.

As various changes could be made in the above constructions without departing from the scope of the invention, it is intended that all matter contained in the above description or shown in the accompanying drawings shall be interpreted as illustrative and not in a limiting sense.

What is claimed is:

1. A plasmonic sensor for the detection of chemical and biological specimens, said plasmonic sensor comprising:

an optical fiber, the optical fiber comprising;

a core;

a cladding; and a polished flat surface of the core formed on a longitudinal side of the optical fiber; and a regular array of nanoantennae formed in a pattern on the polished flat surface of the core formed in the longitudinal side of the optical fiber.

2. The plasmonic sensor of claim 1, wherein the regular array of nanoantennae comprises one of:

a regular array of metalized nano-discs, the regular array of metalized nano-discs being disposed in a pattern on and extending away from the polished flat surface of the core;

a seed layer formed on the polished flat surface of the core, the regular array of metalized nano-discs disposed in a pattern on and protruding upward from the seed layer; and a metalized layer comprising a regular array of metalized holes formed in a pattern in the metalized layer and extending onto the polished flat surface of the core.

3. The plasmonic sensor of claim 2, wherein the optical fiber is embedded in a support base such that the polished flat surface of the core formed on the longitudinal side of the fiber is exposed and coplanar with an upper surface of the support base.

4. The plasmonic sensor of claim 2 wherein the optical fiber is embedded in a sealed housing, the housing comprising a base, a top, and a plurality of side walls that define a fluid inlet, a flow channel, and one or more fluid outlets, such that the regular array of nanoantennae lay within the flow channel, and such that a sample solution containing one or more specimens of interest can flow into the fluid inlet, through the flow channel, over the regular array of nanoantennae, and out the one or more fluid outlets.

5. The plasmonic sensor of claim 4, further comprising one or more pairs of focusing regions arranged on opposing sides of the flow channel, such that, on application of a voltage across any of the one or more pairs of focusing regions, the one or more specimens of interest between the one or more pairs of focusing regions are concentrated along an interior of the flow channel.

6. The plasmonic sensor of claim 5, wherein the plurality of side walls further define one or more waste channels arranged as channels branching off from the flow channel after each of the one or more pairs of focusing regions, such that a flow of excess sample solution can divert into the one or more waste channels.

7. The plasmonic sensor of claim 4, further comprising one or more pairs of trapping regions arranged on opposing sides of the flow channel, wherein the regular array of nanoantennae lay within the flow channel between one of the pairs of trapping regions, such that on application of a voltage across any pair of the one or more pairs of trapping regions, an electric field is generated that impedes flow of the one or more specimens of interest.

8. A plasmonic sensor system for the detection of chemical and biological specimens, said plasmonic sensor system comprising:

plasmonic sensor, the plasmonic sensor comprising:

an optical fiber, the optical fiber comprising;

a core;

a cladding; and a polished flat surface of the core formed on a longitudinal side of the optical fiber;

a regular array of nanoantennae formed in a pattern on the polished flat surface of the core formed in the longitudinal side of the optical fiber;

a laser source structured and operable to generate and provide laser light signal into the first end of the optical fiber;

an optical coupler structured and operable to guide the light signal generated by the laser source into and out of the optical fiber;

an optical detector structured and operable to detect the light signal as it exits the optical fiber; and a computer-based processing system structured and operable to execute analysis software, via a processor, whereby characteristics of the light signal received at the optical detector is analyzed to detect various chemical or biological attributes contained in specimen that has been placed in contact with the plasmonic sensor.

9. The plasmonic sensor system of claim 8 further comprising a support base having an upper surface, wherein the optical fiber is embedded in the support base such that the polished flat surface of the core having formed on the longitudinal side of the optical fiber is exposed and coplanar with the support base upper surface.

10. The plasmonic sensor system of claim 9, wherein the regular array of nanoantennae comprises one of:

a regular array of metalized nano-discs, the regular array of metalized nano-discs being disposed in a pattern on and extending away from the polished flat surface of the core;

a seed layer formed on the polished flat surface of the core, the regular array of metalized nano-discs disposed in a pattern on and protruding upward from the seed layer; and a metalized layer comprising a regular array of metalized holes formed in a pattern in the metalized layer and extending onto the polished flat surface of the core.

11. The plasmonic sensor system of claim 10 wherein the optical fiber is embedded in a sealed housing, the housing comprising a base, a top, and a plurality of side walls that define a fluid inlet, a flow channel, and one or more fluid outlets, such that the regular array of nanoantennae lay within the flow channel, and such that a sample solution containing one or more specimens of interest can flow into the fluid inlet, through the flow channel, over the regular array of nanoantennae, and out the one or more fluid outlets.

12. The plasmonic sensor system of claim 11, further comprising one or more pairs of focusing regions arranged on opposing sides of the flow channel, such that, on application of a voltage across any of the one or more pairs of focusing regions, the one or more specimens of interest between the one or more pairs of focusing regions are concentrated along an interior of the flow channel.

13. The plasmonic sensor system of claim 12, wherein the plurality of side walls further define one or more waste channels arranged as channels branching off from the flow channel after each of the one or more pairs of focusing regions, such that a flow of excess sample solution can divert into the one or more waste channels.

14. The plasmonic sensor system of claim 11, further comprising one or more pairs of trapping regions arranged on opposing sides of the flow channel, wherein the regular array of nanoantennae lay within the flow channel between one of the pairs of trapping regions, such that on application of a voltage across any pair of the one or more pairs of trapping regions, an electric field is generated that impedes flow of the one or more specimens of interest.

15. A method of fabricating a plasmonic sensor for the detection of chemical and biological specimens, wherein the plasmonic sensor comprises an optical fiber having a diameter, a longitudinal side and a core, said method comprising:

polishing a region of the longitudinal side of the optical fiber to generate a flat exposed surface of the core;

applying a layer comprising one or more sequential sublayer of material to the flat exposed surface of the core, wherein the material composition of each of the one or more sequential sublayer is at least one of an electrically conductive material and a semiconductive material, and the layer comprises an uppermost surface;

applying a patternable substrate atop the uppermost surface;

using lithography to pattern an array of holes in the substrate, such that the holes penetrate to the uppermost surface; and one of:

electroplating the uppermost surface with a conductive or semiconductive disc material to generate an array of nanoantennae that are located and defined by the array of holes; and forming nano sized holes in the uppermost surface that are located and defined by the array of holes and that extend at most from the uppermost surface to the flat exposed surface of the core; and removing the patternable substrate.

16. The method of claim 15, wherein the one or more sequential sublayer comprises a first sublayer of chromium and a second sublayer of gold.

17. The method of claim 15, wherein the conductive or semiconductive disc material is gold.

18. The method of claim 15, where in the patternable substrate material is a positive photoresist.

19. The method of claim 18, wherein the lithography is performed by exposing the positive photoresist to an array of self-assembling microspheres and then irradiating the array with light.

* * * * *